US00RE39961E

(19) United States
(12) Reissued Patent
Petrofsky et al.

(10) Patent Number: US RE39,961 E
(45) **Date of Reissued Patent: *Dec. 25, 2007**

(54) COMPUTER CONTROLLED HYDRAULIC RESISTANCE DEVICE FOR A PROSTHESIS AND OTHER APPARATUS

(75) Inventors: Steven H. Petrofsky, Beavercreek, OH (US); William G. Gruesbeck, Beavercreek, OH (US)

(73) Assignee: ÖSSUR hf, Reykjavik (IS)

( * ) Notice: This patent is subject to a terminal disclaimer.

(21) Appl. No.: 10/426,249
(22) Filed: Apr. 29, 2003

Related U.S. Patent Documents

Reissue of:
(64) Patent No.: 6,113,642
Issued: Sep. 5, 2000
Appl. No.: 09/189,233
Filed: Nov. 10, 1998

U.S. Applications:
(63) Continuation of application No. 10/237,571, filed on Sep. 5, 2002, now abandoned, which is a continuation-in-part of application No. 08/883,614, filed on Jun. 26, 1997, now Pat. No. 5,888,212.
(60) Provisional application No. 60/020,904, filed on Jun. 27, 1996.

(51) Int. Cl.

| | |
|---|---|
| ***A61F 2/64*** | (2006.01) |
| ***A61F 2/70*** | (2006.01) |
| ***A61F 2/74*** | (2006.01) |
| ***A61F 2/60*** | (2006.01) |
| ***A61F 2/76*** | (2006.01) |
| | *F16F 9/46; F16F 9/44; A61F 2/50; A61F 2/68* |

(52) U.S. Cl. ..... 623/24; 623/44; 188/282.3
(58) Field of Classification Search .... 623/39–46 FOR, 623/24; 701/78, 83, 85; 188/282.2, 282.3; 482/5, 6
See application file for complete search history.

(56) References Cited

U.S. PATENT DOCUMENTS 3,820,168 A 6/1974 Horvath
3,995,324 A 12/1976 Burch
4,005,496 A 2/1977 Wilkes (Continued)

FOREIGN PATENT DOCUMENTS

| | | | |
|---|---|---|---|
| DE | 3543291 A1 | 6/1987 | ..... 188/282.2 |
| DE | 4229330 | 3/1994 | |
| EP | 0503775 A1 | 9/1992 | |

(Continued)

OTHER PUBLICATIONS

An Auto–Adaptive External Knee Prosthesis, Ari Wilkenfeld & Hugh Herr, Artificial Intelligence Laboratory, MIT, Cambridge, Massachusetts, 3 pages, Sep. 2000.

Biologically inspired autoadaptive control of a knee prosthesis, Air Wilkenfeld, Ph. D., Dissertation Abstract, MIT, Cambridge, Massachusetts, 1 page, Sep. 2000.

(Continued)

*Primary Examiner*—David H. Willse
(74) *Attorney, Agent, or Firm*—Knobbe, Martens, Olson & Bear LLP

(57) ABSTRACT

A computer controlled hydraulic resistance device for apparatus such as a prosthetic knee for above knee amputees, includes a two stage pilot operated solenoid valve connected to control the flow of hydraulic fluid to and from a hydraulic actuator which applies resistance to the prosthetic knee or other apparatus through a coupling. Hydraulic pressure is sensed on the high and low side of the actuator by a spring biased magnet and a magnetically actuated electronic sensor and is used by a micro-controller in a closed-loop manner to compensate automatically for variations in the device and in the hydraulic fluid viscosity. The device also has magnetically actuated electronic sensors which sense positions of the apparatus and feed back to the micro-controller for applying a predetermined resistance profile to the apparatus.

21 Claims, 21 Drawing Sheets

U.S. PATENT DOCUMENTS

| | | | | |
|---|---|---|---|---|
| 4,064,569 | A | 12/1977 | Campbell | |
| 4,065,815 | A | 1/1978 | Sen-Jung | |
| 4,209,860 | A | 7/1980 | Graupe | |
| 4,212,087 | A | 7/1980 | Mortensen | |
| 4,310,932 | A | 1/1982 | Nader et al. | |
| 4,354,676 | A | 10/1982 | Ariel | |
| 4,569,352 | A | 2/1986 | Petrofsky et al. | |
| 4,685,927 | A | 8/1987 | Haupt | |
| 4,711,242 | A | 12/1987 | Petrofsky | |
| 4,711,450 | A | 12/1987 | McArthur | |
| 4,760,850 | A | 8/1988 | Phillips et al. | |
| 4,790,522 | A | 12/1988 | Drutchas | |
| 4,854,428 | A | 8/1989 | Horvath | |
| 4,876,944 | A | 10/1989 | Wilson et al. | |
| 4,893,648 | A | 1/1990 | Horvath | |
| 4,919,418 | A | 4/1990 | Miller | |
| 4,958,705 | A | 9/1990 | Horvath | |
| 5,062,856 | A | 11/1991 | Sawamura et al. | |
| 5,092,902 | A | 3/1992 | Adams et al. | |
| 5,133,774 | A | 7/1992 | Sawamura et al. | |
| 5,181,931 | A | 1/1993 | van de Veen | |
| 5,197,488 | A | 3/1993 | Kovacevic | |
| 5,201,772 | A | 4/1993 | Maxwell | |
| 5,230,672 | A | 7/1993 | Brown et al. | |
| 5,277,281 | A | 1/1994 | Carlson et al. | |
| 5,284,330 | A | 2/1994 | Carlson et al. | |
| 5,336,269 | A | 8/1994 | Smits | |
| 5,383,939 | A | 1/1995 | James | |
| 5,397,287 | A | 3/1995 | Lindfors | |
| 5,398,917 | A | 3/1995 | Carlson et al. | |
| 5,405,409 | A | 4/1995 | Knoth | |
| 5,413,611 | A | 5/1995 | Haslam, II et al. | |
| 5,443,521 | A | 8/1995 | Knoth et al. | |
| 5,472,412 | A | 12/1995 | Knoth | |
| 5,476,441 | A | 12/1995 | Durfee et al. | |
| 5,545,232 | A | 8/1996 | van de Veen | |
| 5,571,205 | A | 11/1996 | James | 623/24 |
| 5,645,590 | A | 7/1997 | van de Veen | |
| 5,645,752 | A | 7/1997 | Weiss et al. | |
| 5,670,077 | A | 9/1997 | Carlson et al. | |
| 5,683,615 | A | 11/1997 | Munoz | |
| 5,704,945 | A | 1/1998 | Wagner et al. | 623/44 |
| 5,711,746 | A | 1/1998 | Carlson | |
| 5,728,170 | A | 3/1998 | Becker et al. | |
| 5,728,174 | A | 3/1998 | Fitzlaff | |
| 5,746,774 | A | 5/1998 | Kramer et al. | |
| 5,749,533 | A | 5/1998 | Daniels | |
| 5,755,813 | A | 5/1998 | Krukenberg | |
| 5,823,309 | A | 10/1998 | Gopalswamy et al. | |
| 5,842,547 | A | 12/1998 | Carlson et al. | |
| 5,888,212 | A | 3/1999 | Petrofsky et al. | 623/24 |
| 5,888,236 | A | 3/1999 | van de Veen | |
| 5,893,891 | A | 4/1999 | Zahedi | |
| 5,900,184 | A | 5/1999 | Weiss et al. | |
| 5,906,767 | A | 5/1999 | Karol et al. | |
| 5,947,238 | A | 9/1999 | Jolly et al. | |
| 5,948,021 | A | 9/1999 | Radcliffe | |
| 5,960,918 | A | 10/1999 | Moser et al. | |
| 5,967,273 | A | 10/1999 | Hampton | |
| RE36,521 | E | 1/2000 | Heimisch | |
| 6,027,664 | A | 2/2000 | Weiss et al. | |
| 6,095,486 | A | 8/2000 | Ivers et al. | |
| 6,113,642 | A | 9/2000 | Petrofsky et al. | |
| 6,117,177 | A | 9/2000 | Chen et al. | |
| 6,139,586 | A | 10/2000 | Wagner et al. | |
| 6,168,634 | B1 | 1/2001 | Schmitz | |
| 6,352,144 | B1 | 3/2002 | Brooks | |
| 6,423,098 | B1 | 7/2002 | Biedermann | |
| 6,443,993 | B1 | 9/2002 | Koniuk | |
| 6,517,585 | B1 | 2/2003 | Zahedi et al. | |
| 6,679,920 | B2 | 1/2004 | Biedermann et al. | |
| 6,695,885 | B2 | 2/2004 | Schulman et al. | |
| 6,719,806 | B1 | 4/2004 | Zahedi et al. | |
| 6,764,520 | B2 | 7/2004 | Deffenbaugh et al. | |

FOREIGN PATENT DOCUMENTS

| | | | | |
|---|---|---|---|---|
| EP | 549855 | | 9/1992 | |
| EP | 0628296 | A2 | 12/1994 | |
| EP | 1125825 | A2 | 8/2001 | |
| FR | 2623086 | | 5/1989 | |
| GB | 2 201 260 | A | 8/1988 | |
| GB | 2 244 006 | A | 11/1992 | |
| GB | 2268070 | | 1/1994 | |
| GB | 2 328 160 | | 2/1999 | |
| GB | 2 334 891 | | 8/1999 | |
| GB | 2 338 653 | | 12/1999 | |
| JP | 60-81530 | | 5/1985 | |
| JP | 03181633 | A | 7/1991 | |
| JP | 3-181633 | | 8/1991 | 188/282.3 |
| JP | 4-78337 | | 3/1992 | 188/282.3 |
| JP | 04078337 | A | 12/1992 | |
| WO | WO 96/41599 | | 12/1996 | |
| WO | WO 99/08621 | | 2/1999 | |
| WO | WO 99/29272 | | 6/1999 | |
| WO | WO 02/080825 | A2 | 10/2002 | |

OTHER PUBLICATIONS

Otto Bock Orthopadische Industrie, C–LEG A new dimension in amputee mobility, Otto Bock 1997 (4 pages).

State–Of–The–Art Prosthetic Leg Incorporates Magneto–Rheological Technology, Medical Product Manufacturing News, p. 42, Nov. 2000.

"Optimal Control For An Above–Knee Prosthesis With Two Degrees Of Freedom", D. Popovic et al, 1995, pp. 89–98, J. Biomechanics, vol. 28, No. 1.

"Design Principles, Biomedical Data and Clinical Experience with a Polycentric Knee Offering Controlled Stance Phase Knee Flexion: A Preliminary Report", Siegmar Blumentritt, Ph. D. et al 1997, Journal of Prosthetics and Orthotics, vol. 9, No. 1, 18–24.

COMPUTER CONTROLLED HYDRAULIC RESISTANCE DEVICE FOR A PROSTHESIS AND OTHER APPARATUS

Matter enclosed in heavy brackets [ ] appears in the original patent but forms no part of this reissue specification; matter printed in italics indicates the additions made by reissue.

RELATED APPLICATION

[This application is a continuation-in-part of application Ser. No. 08/883,614, Filed Jun. 26, 1997, now U.S. Pat. No. 5,888,212. This application also claims the benefit of prior application Ser. No. 60/020,904, Filed Jun. 27, 1996.] *This application is a continuation of application 10/237,571, filed 5 Sep. 2002 (abandoned), which is a reissue of U.S. Pat. No. 6,113,642, issued 5 Sep. 2000, which is a continuation-in-part of application 08/883,614, filed 26 Jun. 1997 (now U.S. Pat. No. 5,888,212), which claims the benefit of provisional application 60/020,904, filed 27 Jun. 1996.*

BACKGROUND OF THE INVENTION

The present invention is ideally suited for use with an artificial leg or prosthesis worn by an above knee amputee, but also has other applications and uses. Normally this type of prosthesis involves an artificial knee joint including a socket for receiving and engaging the stump of the user, a knee bracket rigidly connected to the socket, and a frame which extends downwardly from the bracket and is pivotally connected to the bracket by a horizontal shaft. A pylon and artificial foot are connected to the base of the frame, and a control unit is connected for locking the knee joint to prevent it from buckling under load in the stance phase of a step, and for freeing the knee joint in the swing phase of the step. Preferably, the prosthesis controls the knee joint in such a way that the amputee will walk with a normal or natural appearing gait. This gait is characterized by almost identical movements performed by both lower limbs at varying walking speeds.

The biological or natural knee joint is powered by the actions of muscles. Each muscle develops an active force by contraction and also provides variable stiffness or resistance. It has not been feasible to duplicate muscle contraction in leg prosthesis because of the weight and bulk that would be required to duplicate this function. Research has focused on implementing stiffness or resistance to rotation of the knee joint. Usually this involves switching the knee joint between one of two modes, locked or free to rotate. The locked mode occurs during the stance phase of the gait cycle, and the free to rotate mode occurs during the swing phase of the gait cycle. The stance phase applies when the foot of the prosthesis is on the ground, and the swing phase applies during the time when the foot of the prosthesis is off the ground.

Much of the research in recent years has sought improvements in controlling an artificial knee joint as a way to improve gait and enable the amputee to deal with situations such as descending stairs or ramps, or lowering into a sitting position. If a knee joint is considered a simple hinge, there are two separate actions which occur. During flexion, the upper and lower segments move closer together during rotation of the knee joint. During extension, the leg straightens and the segments move apart. For a prosthetic knee joint to duplicate a biological knee, it is necessary to control the resistance to rotation in each direction independently and variably. This resistance to rotation during swing phase can be accomplished with a mechanical damper or friction device, a pneumatic damper, or a hydraulic damper. It is generally accepted in prosthetics that a hydraulic damper provides the smoothest action over a wider range of walking speeds.

Stance phase control must provide a very high resistance to flexion or lock completely any rotation to flexion. Stance control is usually provided by a weight activated mechanical locking brake mechanism, or a position activated polycentric linkage system, or a position activated hydraulic damper. Mechanical braking mechanisms can be difficult to keep adjusted properly and can cause the amputee to walk with a slightly unnatural gait. Position activated polycentric mechanisms require more concentration and can be difficult for amputees to use in some situations. Hydraulic dampers, while providing a more natural gait, require more concentration and training for the amputee.

U.S. Pat. Nos. 5,405,409 and 5,443,521, which issued to the assignee of the present invention, disclose a linear type hydraulic damper for controlling an above knee prosthesis. This hydraulic damper has independently adjustable and variable resistance in flexion and extension during the swing phase of the gait cycle. Because of the turbulent flow of the hydraulic fluid during the swing phase, this damper can accommodate a wide variation of gait speeds. The control damper has a single damping rate in stance phase that can be manually adjusted for each amputee's need. When the knee joint is fully extended, the damper assumes a non-stance resistance mode. This position activated stance phase can initially require extra gait training and concentration on the part of the amputee to receive full benefit of the damper.

Electronics have recently been introduced into lower extremity prosthetics in an attempt to make walking easier for the amputee. For example, U.S. Pat. No. 5,062,856 and U.S. Pat. Nos. 5,383,939 and 5,571,205 disclose two systems which use a microprocessor control to adjust the resistance in a pneumatic or hydraulic cylinder during swing phase in an attempt to provide control of rotation of the knee joint over a wider range of walking speeds than is available with standard pneumatic or friction dampers.

Further improvement in amputee gaits could come from a mechanism that in the beginning of the stance phase would allow for a small amount of knee flexion and then lock against further flexion while simultaneously allowing for knee extension as the leg straightens due to body action. Such a mechanism is described by Siegmar et al in "Design Principles, Biomechanical Data and Clinical Experience with a Polycentric Knee Offering Controlled Stance Phase Knee Flexion: A Preliminary Report", Journal of Prosthetics and Orthotics, Vol. 9, No. 1, pp. 18–24, Winter 1997, and by Popvic et al in "Optimal Control for an Above-knee Prosthesis with Two Degrees of Freedom", J. Biomechanics, Vol. 28 No. 1, pp. 89–98, 1995.

An amputee needs different resistance to knee flexion during stair descent than is needed while sitting down in a chair. Accordingly, it is desirable for a control mechanism to be capable of providing these different resistances to knee flexion automatically. The control mechanism should also provide for swing resistance over a wide range of gait speeds. All of this should happen automatically so that the amputee can walk without having to think about his prosthesis.

The same type of computer controlled hydraulic damper system that can be used with amputees can also be used on other applications such as robotics, braking systems, and exercise equipment. These applications only vary in the size of the actuator to control the maximum resistance applied.

They all may use common sensors, microprocessor controlled electronics, and valve technology. Computer controlled exercise equipment are disclosed in U.S. Pat. Nos. 4,354,676, 4,711,450, 4,919,418, 5,230,672, and 5,397,287. In any such equipment, it is desirable to be able to maintain accurate applied resistance over a wide range of temperature and manufacturing tolerances. It is also desirable to have proper feedback control and a hydraulic valve and controller designed for relatively slow speeds of operation.

SUMMARY OF THE INVENTION

The present invention is directed to a computer controlled closed-loop electromechanical resistance device. One application of the device is to provide swing resistance to the knee unit of a lower limb prosthesis as worn by an above-knee amputee. Other applications for the invention include rehabilitation equipment, exercise equipment, braking devices or other various damping applications.

In accordance with a preferred embodiment of this invention, the device comprises a rotary paddle or vane type rotor or actuator. When the rotary vane is rotated, hydraulic fluid is forced through an electronically controlled valve from one side of the vane to the opposite side of the vane. As rotation is reversed, the hydraulic fluid reverses direction and flows back through the same valve. Computer control of the valve creates a variable pressure differential from one side of the rotary vane to the other side. The variable pressure differential is sensed as a variable resistance on the rotary vane. However, the resistance device of the invention may also be utilized with a linear type of actuator with equal effectiveness.

The valve used in one embodiment of the device is a proportional controlled, solenoid actuated, balanced spool valve. The shape of the spool is such that flow across the face of the spool has little or no effect on spool movement, thus eliminating any possibility of unbalanced flow induced forces. The valve spool is also pressure balanced to eliminate any possibility of a hydraulic lock. The magnetic core for the valve is shaped to produce a near constant force in the working stroke of the spool when constant power is supplied. In another embodiment, a two stage poppet or pilot operated valve is used to increase the servo valve dynamic range and to reduce significantly the unbalanced forces applied. Valve control includes a high frequency dithering to avoid spool drag, and proportional control is provided to minimize wear rate as normally associated with a pulse width modulated control.

The valve control used in the device is a microprocessor based closed loop adaptive control. The microprocessor reads actuator or rotor vane pressure differential, rotor position, auxiliary force and pressure differential error at 1–5 ms intervals (200–1000 Hz). The microprocessor calculates rotor position, rotor velocity, and rotor direction at 10–25 ms intervals (40–100 Hz). Based on this information, the microprocessor calculates the required rotor resistance (pressure differential) based on state equations, thus creating an automatically adjusting resistance device. If the difference between the actual and required pressure differential is large, the microprocessor changes the valve in large increments to compensate for this large error. If the difference between the actual and required pressure differential is small, the microprocessor changes the valve in smaller increments to compensate for this small error. By utilizing pressure feedback for the closed loop control, the control system is able to compensate automatically for machining tolerances, valve solenoid resistance variations, different fluid viscosity, temperature effects and wear. Constants in the state equations adapt with changes in the system operating environment for adaptive control.

When the device of the invention is used as a knee control unit for an above knee amputee, the control unit detects five significant points in a typical gait cycle. The two major areas of a gait cycle are stance phase and swing phase. Stance phase is the time in which the prosthesis is in contact with the ground. Swing phase is the time in which the prosthesis is not in contact with the ground. The first major point considered is heel strike which is the beginning of the stance phase. This is the point at which the prosthesis first contacts the ground and is no longer swinging in the air. The prosthesis must have stability at this point so that it will not collapse as the amputee's weight is transferred from the opposite leg.

A yielding stance is ideal for this situation in which a high resistance is applied to support the amputee, but allowing the prosthesis to flex slightly. Ideally, the prosthesis should flex about ten degrees so that the amputee does not have to vault over a fully extended prosthesis. This ten degree flexion during stance is the second point of consideration. At this point, the prosthesis begins to extend as the amputee propels himself forward. The prosthesis fully extends during this propulsion. After propulsion, the third point is the initiation of flexion in which the amputee begins to move the prosthesis forward by flexing of the hip. The fourth point is toe off in which the prosthesis leaves the ground. This is the start of swing phase.

During the swing phase, the knee control unit offers significant resistance to limit the swing speed and the amount of angular movement of the lower section of the prosthesis. Ideally, the knee should flex no more than sixty-five degrees during swing phase. This may be achieved by introducing a high resistance to limit the amount of heel rise. Due to the momentum of the prosthesis, the knee control unit begins to extend while swinging through the air. The fifth point of consideration is terminal deceleration. This occurs just prior to flee strike during the final few degrees of extension in which a high resistance must be applied to limit any harsh knee slap as the prosthesis contacts the extension stops.

To control the knee control unit, the microprocessor of the invention reads rotor vane pressure differential, knee position, pressure differential error and prosthetic force at 1–5 ms intervals (200–1000 Hz). The microprocessor calculates the knee position, knee velocity, knee direction and reads user settings (1–10) for flexion and extension at 10–25 ms intervals (40–100 Hz). The user settings for flexion and extension set an area for use, and the adaptive control fine tunes the unit from this baseline. Based on this information, the microprocessor calculates the required knee resistance (pressure differential) required based on state equations, thus creating an automatically adjusting knee control unit.

Constants in the state equations are able to adapt with changes in the system operating environment. If the difference between the actual and required pressure differential is large, the microprocessor changes the valve in large increments to compensate for this large error. If the difference between the actual and required pressure differential is small, the microprocessor changes the valve in smaller increments to compensate for this small error. If the knee angle is extending and nearing full extension, the microprocessor starts to close the valve to create a high resistance and slow the prosthesis in the extension direction. When the knee angle is flexing and nearing the ideal heel rise, the microprocessor starts to close the valve to create a high resistance and slow the prosthesis in the flexion direction. The prosthetic measured force allows the microprocessor to distinguish between heel strike, mid-stance, or toe off. This aids the amputee in descending stairs by creating a high knee resistance and lowering the amputee to the next stair by using his own weight.

Stumble recovery is achieved by sensing force and knee pivoting velocity. If the force sensors indicate a stance phase and knee velocity is high, this might indicate a stumble condition so that the system imposes a high resistance to help the amputee regain control. In the case of prolonged nonuse of greater than 5 seconds, the microprocessor reverts to sleep mode in which all components are shut down except the knee angle sensor circuit. This conserves battery power, but permits the control system to resume with a change in knee angle. Power is supplied to the control system by four 3.6 volt lithium ion batteries in a replaceable battery pack which is rechargeable to ninety percent capacity in two hours. Battery lift is approximately thirty hours between full recharges.

Preferably, the knee control unit operates with a rotary vane rotor positioned inside a rotor housing on the knee axis, and the knee bracket is connected to the rotary vane. As the knee is flexed, the vane rotates forcing hydraulic fluid out of the chamber through the solenoid control valve which in turn controls the fluid flow and pressure. This control of the fluid flow and pressure provides the resistance available at the knee axis. Fluid exiting the solenoid control valve flows through a weight actuated stance valve. This valve limits fluid flow whenever weight is applied to the prosthesis. The stance valve is adjustable to allow various yielding rates depending upon the amputees weight or preference. Fluid exiting the stance valve enters an extension bias cylinder. This cylinder consists of a spring loaded piston which is compressed when the knee control unit is flexed. Fluid on the opposite side of the bias piston is directed to the opposite side of the rotary vane, thus completing the fluid path. During extension, the flow is reversed with the stored potential energy of the spring biased piston available to assist in extending the prosthesis.

Other features and advantages of the invention will be apparent from the following description, the accompanying drawings and the appended claims.

DESCRIPTION OF THE PREFERRED EMBODIMENTS

Figure 1:
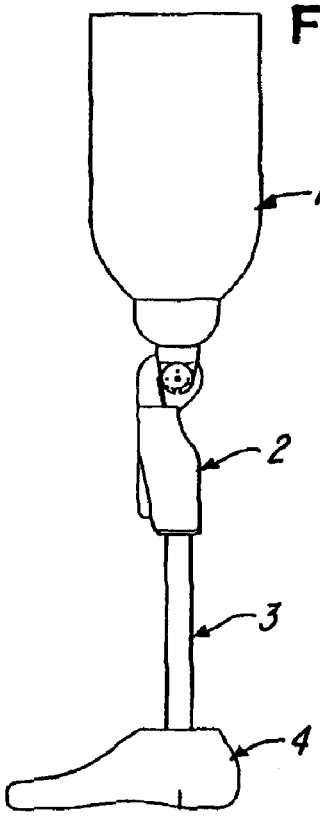
FIG. 1 is a side elevation view of a lower limb prosthesis for an above-knee amputee and incorporating a resistance device or knee control unit constructed in accordance with the invention.
Figure 2:
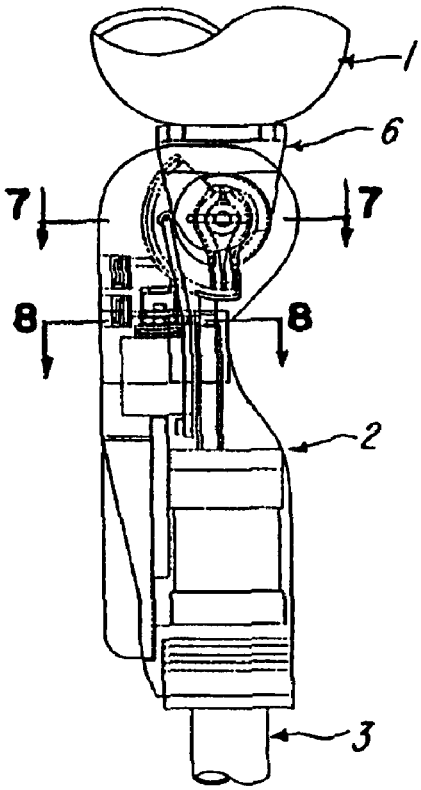
FIG. 2 is an enlarged fragmentary side view of the knee control unit shown in FIG. 1.
Figure 3:
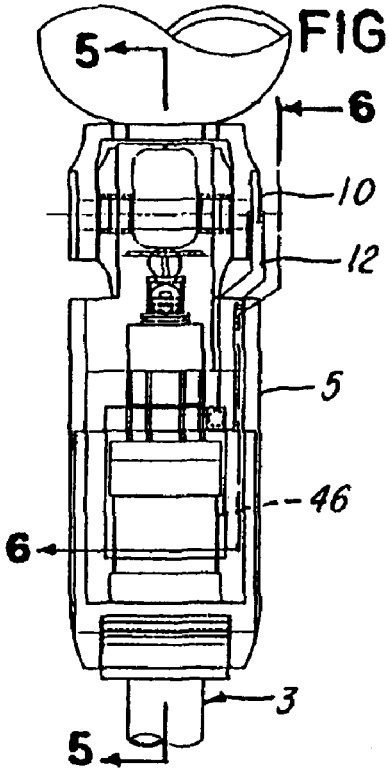
FIG. 3 is the front view of knee control unit.
Figure 4:
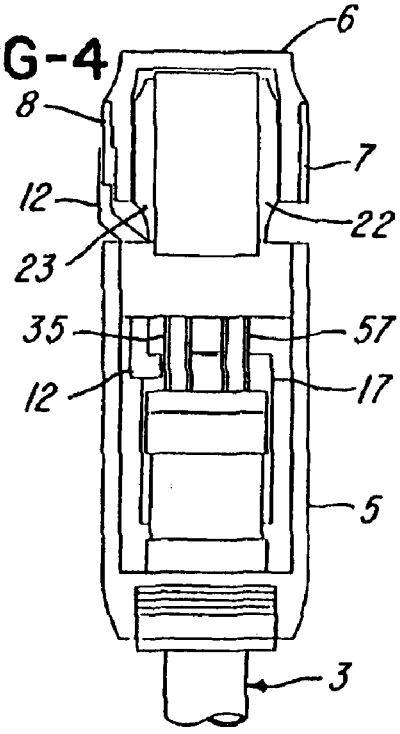
FIG. 4 is the rear view of knee control unit.

In reference to FIG. 1, a typical lower limb prosthesis for an above-knee amputee includes a residual limb socket 1 which functions as an interface between the amputee and the prosthesis, a knee control assembly or unit 2 which provides knee rotation and resistance to aid in walking, a mounting pylon 3 and a foot 4. The components 1, 3 and 4 are conventional and commercially available.

The knee control assembly or unit 2 is described in connection with FIGS. 2–14 and includes a frame assembly 5 and an inverted U-shaped knee bracket 6 secured to the socket 1. The knee bracket 6 includes a right side retainer plate 7 and a left side retainer plate 8. The knee bracket 6 slides over opposite end portions of a rotor shaft 9 (FIG. 5), and each end portion has parallel flats to key the shaft to the bracket. The side retainer plates 7 and 8 are secured to the bracket 6 by screws, and the shaft 9 rotates with the knee bracket 6 relative to the frame 5. The left side retainer plate 8 also has an outer cam surface (FIG. 6) to actuate a knee angle sensing mechanism.

Figure 6:
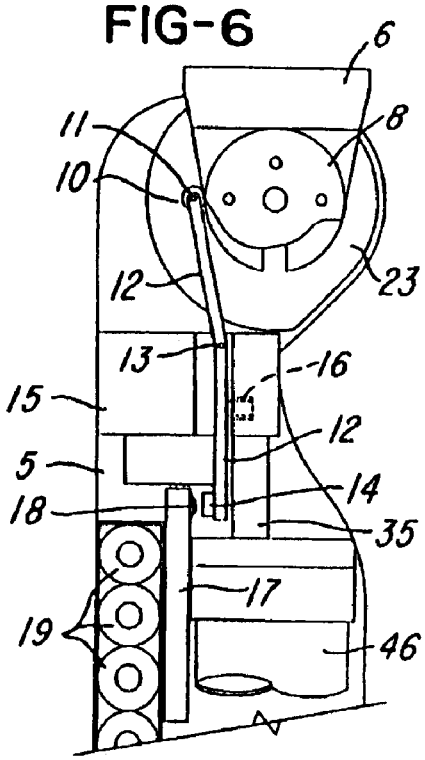
FIG. 6 is a part section taken generally on the line 6—6 of FIG. 3 and showing a knee angle sensing mechanism.

FIG. 6 shows the knee angle sensing mechanism which includes a roller 10 attached to a knee angle lever arm 12 with a pin 11. The knee angle lever arm 12 pivots on a cross pin 13 which is pressed into a housing 15. A magnet 14 is attached to the lower end of the knee angle lever arm 12 with adhesive. As the knee bracket 6 rotates relative to the housing 15 and frame 5, the roller 10 rides on cam surface of the left side retainer plate 8. A spring 16 causes the lever arm 12 to pivot on pin 13 which in turn varies the distance between the magnet 14 and a Hall effect sensor 18 mounted on a PC board assembly 17. As this distance is varied, the output of the Hail effect sensor 18 varies to indicative the true knee angle of the frame 5 and housing 15 relative to the bracket 6. Power is supplied to the PC board 17 by a multiple battery pack 19.

Figure 5:
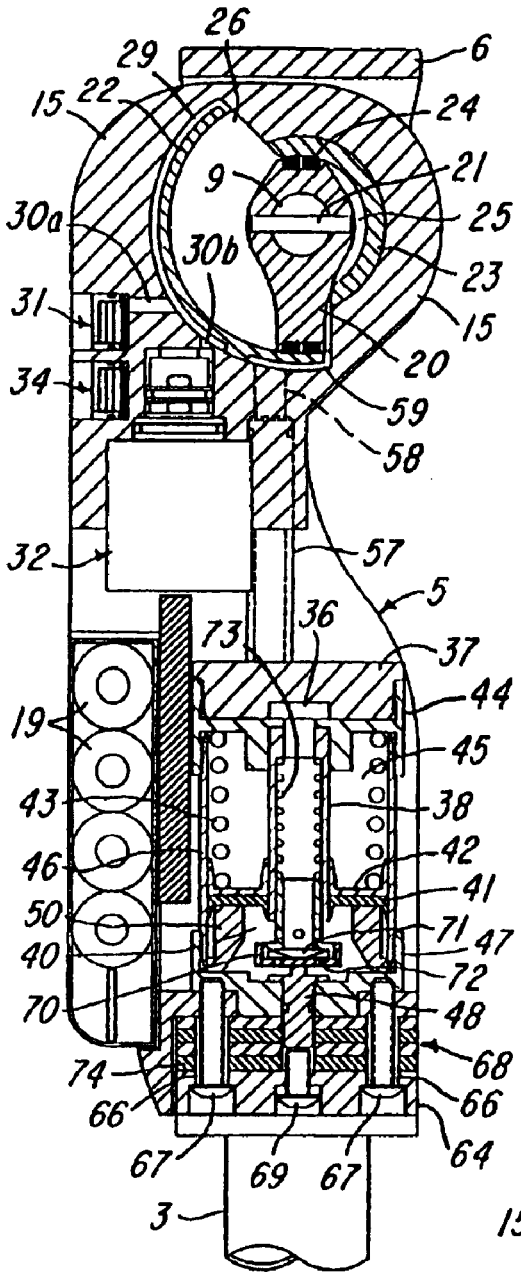
FIG. 5 is a section taken generally on the line 5—5 of FIG. 3 and showing internal components.
Figure 7:
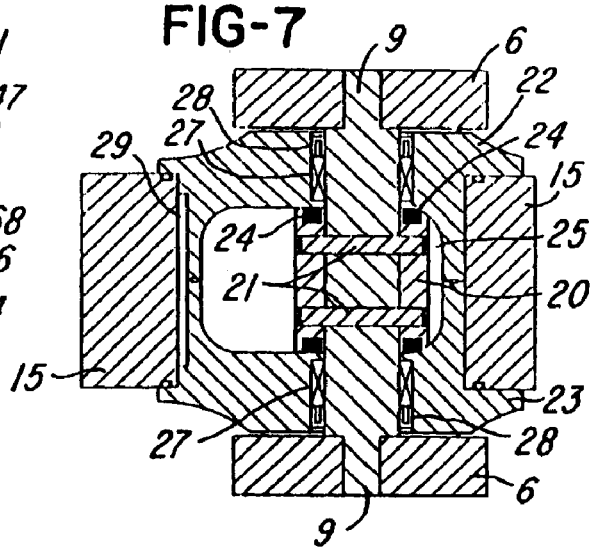
FIG. 7 is a section taken generally on line 7—7 of FIG. 2 and showing the resistance rotor and rotor housing.

FIG. 5 shows the internal components of the knee control unit or assembly 2. Hydraulic fluid is the working fluid that provides for knee control resistance. Resistance is provided to the knee bracket 6 via the rotor shaft 9 (FIG. 7), and a vane-type rotor 20 (FIGS. 5, 7, 13A–13C) is attached to the rotor shaft by two cross pins 21. The rotor chamber is defined by a right side rotor housing or cap 22 (FIG. 7) and a left side rotor housing or cap 23. Two endless Teflon seals 24 seal the rotor 20 against the rotor caps 22 and 23, thereby creating two separate rotor chambers 25 and 26 (FIG. 5). As shown in FIG. 7, the rotor shaft 9 is supported by roller bearings 27 to support the amputee's weight, while side thrust loads are supported by flat Teflon thrust washers between the caps 22 and 23 and the sides or leg of the bracket 6. The rotor shaft 9 is sealed against hydraulic fluid leakage with spring biased lip seals 28 adjacent the bearings 27.

Figure 8:
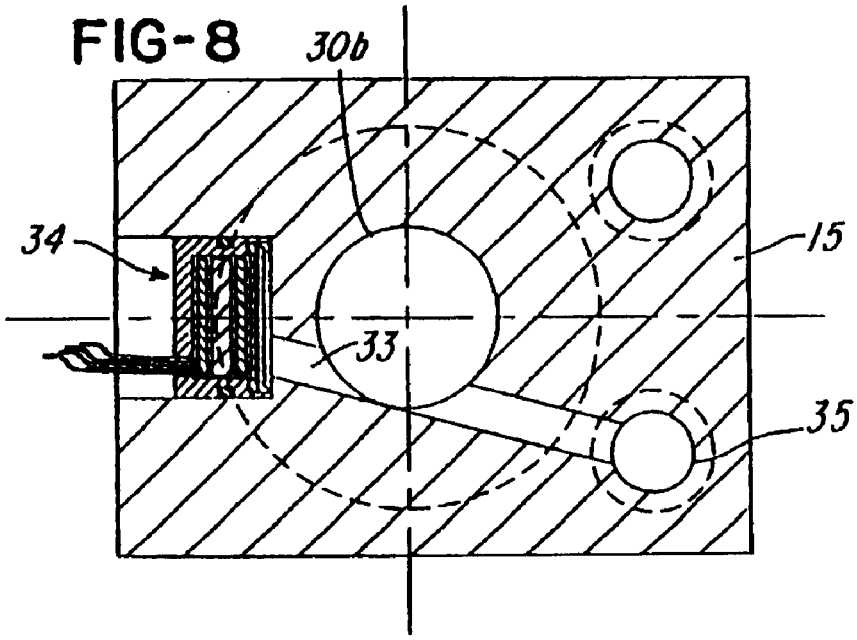
FIG. 8 is a section taken generally on the line 8—8 and showing an extension pressure sensor.

During knee flexion, the rotor 20 is rotated with the knee bracket 6 and rotor shaft 9, thus forcing hydraulic fluid out of rotor chamber 26 (FIG. 5) and through an arcuate passage 29 which is defined between the rotor caps 22 and 23 and the housing 15. From passage 29, the hydraulic fluid is forced into passages 30a and 30b. Passage 30a connects with a flexion pressure sensor 31 which is sealed by an O-ring and retained by a retaining ring. Passage 30b feeds into a valve cavity. Fluid passages 30a and 30b and the valve cavity are machined into the housing 15. From the passage 30b, the hydraulic fluid passes through a solenoid control valve 32 which electronically controls the flow and pressure of the hydraulic fluid in the working chambers 25 and 26. Hydraulic fluid exits the solenoid control valve 32 and enters a fluid passage 33 (FIG. 8).

Passage 33 extends to an extension pressure sensor 34 (FIGS. 5 & 8) which is also sealed by an O-ring and retained with a retaining ring within the housing 15. The passage 33 is also connected to a bias tube 35 (FIG. 4), and hydraulic fluid travels through the bias tube 35 and into a cavity 36 (FIG. 5) which is machined into an upper bias cap 37. Hydraulic fluid then travels through a stance valve tube 38 and a tubular stance valve member 39 into a chamber 40. Fluid flowing into chamber 40 pressurizes an annular seal 41 and an adjacent annular piston 42 which moves upwardly to compress a bias spring 43 which is seated against a spring seat member 44 secured to the cap 37. The spring 43 is located in an oil chamber 45 defined by a cylinder 46 which is secured to a lower cap member 47 supporting a stance valve plunger 48 for axial movement.

An annular support 50 defines the chamber 40 and forms a bottom seat for the annular seal 41 and piston on the stance valve tube 38 which has an upper end pressed into a hub on the spring seat member 44. Bias cylinder leakage is controlled by a series of O-rings (FIG. 5), and hydraulic fluid is forced upwardly out of chamber 45 in response to upward movement of the annular piston 42. The fluid travels through ports within the spring seat member 44 and the upper cap 37, through a return tube 57 (FIG. 4) and passages 58 and 59 into the rotor chamber 25 thus creating a flow loop. Passage 58 is machined into the resistance housing 15, and the arcuate passage 59 is defined between the rotor caps 22 and 23 and the resistance housing 15 and is sealed by suitable O-rings. A spring loaded pressure relief valve (not shown) may be incorporated into the upper bias cap 37 to allow hydraulic flow from the bias tube 35 directly to the return tube 57 in case extremely high fluid pressure is encountered due to rapid flexion. During extension, the flow is reversed due to the rotor 20 moving the hydraulic fluid out of chamber 25 and back through the system. In this case, the bias spring 43 assists in moving the flow from below the piston 42 to the chamber 26, thus ensuring complete extension of the prosthesis.

During the stance phase of gait, the amputees weight is applied to the bottom of the knee control unit 2 at a bottom plate 64 (FIG. 5) through the pylon 3 and foot 4. The bottom plate 64 is retained by tubular sleeves 66 and screws 67. The bottom plate 64 is also supported by a force sensor 68 and an elastomeric pad 74. The elastomeric pad 74 will deform allowing the bottom plate 64 and a stance adjusting screw 69 to move vertically by a slight distance. The elastomeric pad 74 may be effectively replaced with springs, Belleville washers or wave washers while still retaining the same actuation characteristics. The stance adjusting screw 69 actuates the stance valve plunger 48 which pushes on a stance valve cap 70 to move the stance valve 39 upwards into the stance valve tube 38 for closing off the radial ports in the stance valve 39. With these ports closed, the knee control unit will be restricted from any flexion movement.

By adjusting the stance adjusting screw 69, the radial ports in the stance valve cap 70 may be adjusted to limit the closing of the ports during stance thus allowing a controlled leakage in the flexion direction giving the amputee a yielding stance. Extension is not affected during stance due a Belleville washer 71 above a stance check valve washer 72 that covers axial ports in the stance valve cap 70. When extension is performed during the stance phase, the hydraulic flow lifts the stance washer 72 while compressing the Belleville washer 71 to uncover the axial ports in the stance valve cap 70. When flexion is attempted during stance, hydraulic pressure will force the stance washer 72 to cover the holes in the stance valve cap 70 thus prohibiting any flexion flow moving through the stance valve end cap 70. When the load is removed from the bottom plate 64, the stance valve 39 is forced into the open position (FIG. 5) by a return spring 73 within the tube 38 to allow flow to continue through the chamber 40.

Figure 14:
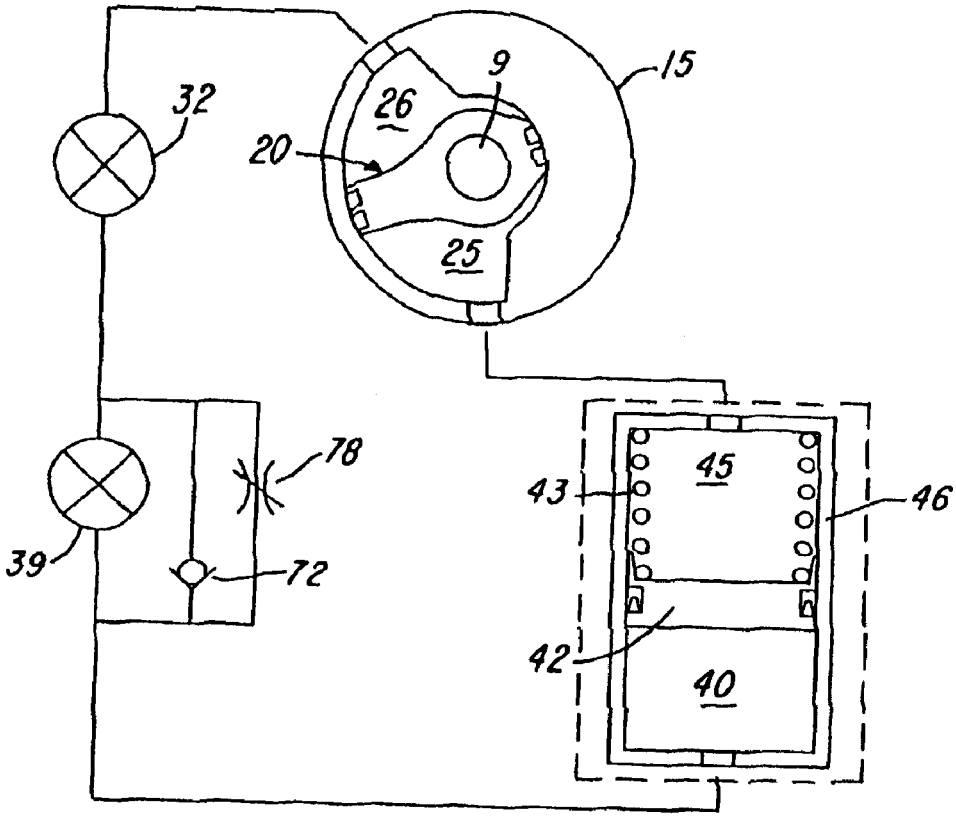
FIG. 14 is a block diagram of the hydraulic circuit for the knee control unit.

A block diagram for generally illustrating the hydraulic system is shown in FIG. 14. By turning the rotor 20 clockwise within the housing 15, hydraulic fluid from chamber 26 is forced through a port to the solenoid control valve 32. The solenoid control valve 32 is electronically operated for variably changing the flow area of the fluid path. By reducing the flow area in the valve 32, the hydraulic flow is reduced while back pressure is increased. This is felt as rotational resistance on the rotor shaft 9. Fluid exits the solenoid control valve 32 through a passage which leads to the stance valve member 39.

The stance valve 39 is actuated when an external force is applied. In parallel with the stance valve 39 is the check valve 72 which prevents flow with clockwise rotation of the rotor 20 when the stance valve 39 is actuated while still allowing flow with counterclockwise rotation. Also in parallel with the stance valve 39 is an adjustable orifice 78 which allows a small controlled flow during clockwise rotation when the stance valve 39 is actuated. Hydraulic fluid exits the stance valve 39 through the radial ports which permits the fluid to move or actuate the piston 42.

The piston 42 separates two chambers 40 and 45 in the cylinder 46. As fluid enters chamber 40, the piston 42 compresses the spring 43. The piston then forces fluid in chamber 45 to exit the cylinder 46. This flow returns to rotor chamber 25 to rotate the rotor clockwise. When the clockwise rotation of the rotor 20 and shaft 9 is released, the bias spring 43 and piston 42 force the hydraulic fluid out of the chamber 40 through the stance valve 39 and back through the solenoid control valve 32 and into chamber 26 resulting in a counterclockwise rotation of the rotor 20 and rotor shaft 9.

Figure 13A:
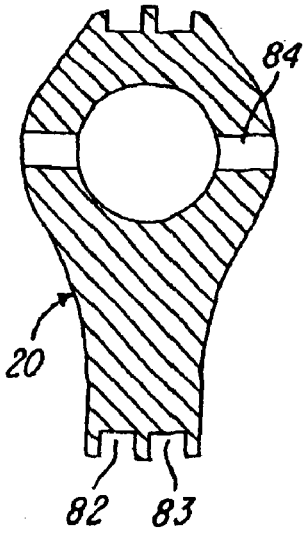
FIGS. 13A–13C are views of the resistance rotor shown in FIGS. 5 & 7.
Figure 13B:
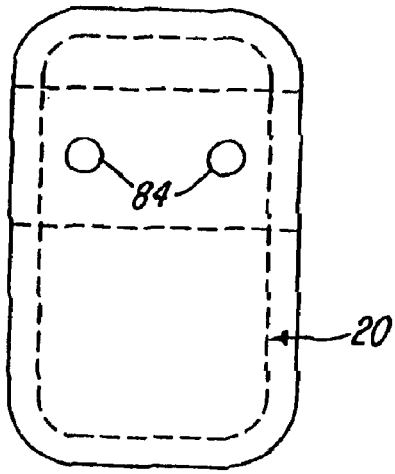
Figure 13C:
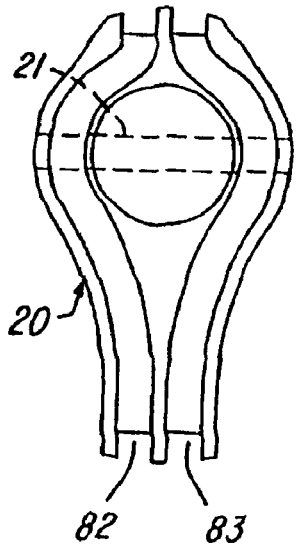

FIGS. 13A–13C show the rotor 20 and its construction. The rotor 20 has two endless grooves 82 and 83 for receiving the endless seals 24. The seals 24 of choice are extruded lathe cut Teflon faced seals, although molded elastomer lip seals will give similar results. Each endless seal is seamless and encompass the full perimeter of the rotor 20. This type of sealing has the advantage of double wiping the sealing surface and as a preseal to the seals 28 (FIG. 7) around the shaft 9 adjacent the legs of the bracket 6 to minimize any external leakage. Two holes 84 (FIGS. 13A & 13B) are provided in the middle of the rotor 20 for receiving the pins 21 which secure the rotor 20 to the rotor shaft 9.

Figure 9:
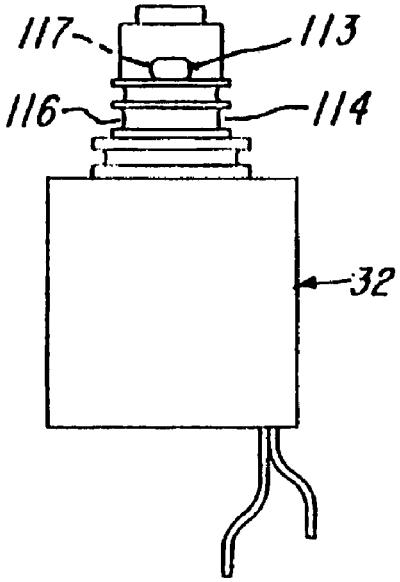
FIG. 9 is an elevational view of a solenoid control valve.
Figure 10:
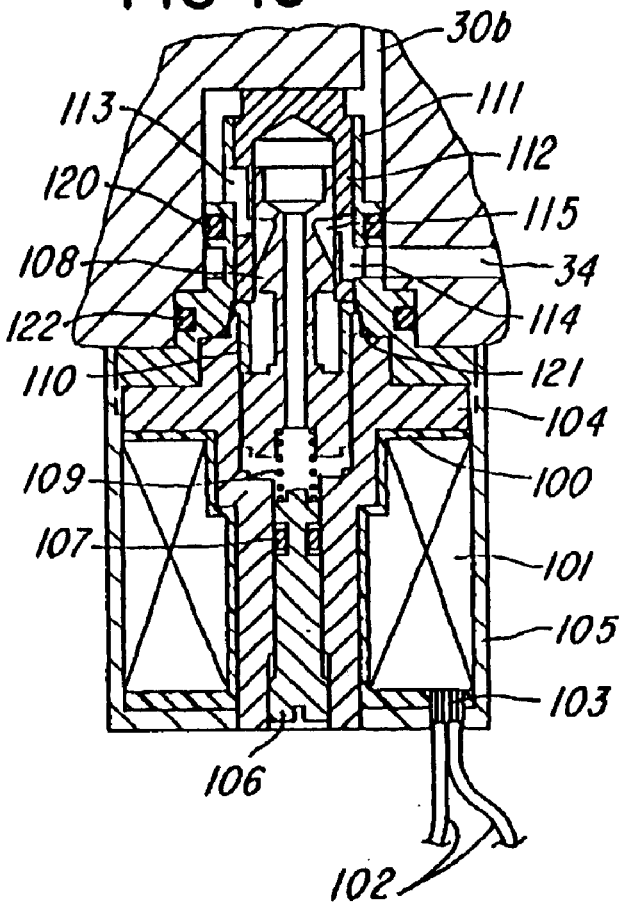
FIG. 10 is an axial section of the solenoid control valve shown in FIG. 9.

An exterior view of the solenoid control valve 32 is shown in FIG. 9 and a cross-sectional view of the solenoid control valve 32 is shown in FIG. 10. A coil bobbin 100 is wound with a wire coil 101 with a radial step. The number of turns in the coil wire 101 is dependent upon the desired electrical and magnetic characteristics desired to operate the valve. Lead wires 102 are attached to the coil wires, and epoxy 103 is applied for strain relief. A flux core 104 is inserted through the center of the bobbin 100, and a metal cup-like case 105 receives the bobbin 100, coil 101 and the flux core 104. An adjusting screw 106 is threaded into the center of the flux core 104 and is sealed with an O-ring 107.

A valve member or valve spool 108 seats on top of a return spring 109, and a tubular spool seat 110 rests on the flux core 104 and is held in place by a tubular cartridge 111. The spool seat 110 limits the travel or axial movement of the spool 108. A cartridge plug 112 is pressed into the cartridge 111 which is threaded into the case 105. A magnetic material, such as low carbon steel, is used for the flux core 104, case 105, adjusting screw 106 and spool 108. These metal parts are preferably hyper annealed for best performance. A nonmagnetic material, such as a 300 series stainless steel, is used for the spool seat 110, cartridge plug 112 and the cartridge 111.

The solenoid control valve 32 is normally open when no power is applied to the coil 101. As power is applied, the coil 101 produces a magnetic flux which pulls the spool 108 further into the flux core 104 against the increasing force of the spring 109. The specific shape of the flux core 104 and spool 108 along with the spring rate of the spring 109 is such that spool movement is proportional to the power applied, this translates to a proportional flow control. As hydraulic fluid enters passage 30b from chamber 29, the fluid is directed from port 113 to port 114 which are formed by the cartridge 111 and the cartridge sleeve 112. If the coil 101 is fully energized, the spool 108 will close off ports 113, 117 and 114 and 116 and the flow will stop. If the coil 101 is partially energized or non-energized, the flow will then enter the spool chamber 115, flow around the spool 108 and exit through port 114 and passage 34 to tube 35.

The pair of ports 113 and 117 and the pair of ports 114 and 116 are at the same level with the ports of each pair spaced 180 degrees from each other, and with each pair of ports spaced 90 degrees from the other pair. The solenoid control valve 32 has two inlet ports 113 and 117 and two outlet ports 114 and 116, although more ports may be used if desired. Although ports 113 and 117 are described as the inlet, and ports 114 and 116 are described as the outlet, the flow may be unidirectional or bidirectional with the same results. The shape of the spool 108 in the flow area 115 provides for counterbalancing any fluid forces that may tend to open or close the spool. The spool 108 has an axial bore or hole through its center to prevent hydraulic lock. The advantages of an optimized magnetic flux to match the spring rate and an optimized spool to match fluid forces greatly reduces the power required to operate the valve. Leakage between the inlet and outlet ports is controlled by O-ring 120 mounted on the cartridge 111. External leakage of hydraulic fluid is controlled by O-rings 121 and 122. Although the solenoid control valve 32 is preferably proportionally controlled, it may also be operated with pulse width modulation.

As mentioned above, the computer controlled hydraulic resistance device of the invention has many applications, such as the knee control described above for above-knee amputees, advanced exercise systems using computer controlled resistance, and robotics or damper applications. While a complete application of an electronic knee control is disclosed herein, the use of the device in other applications is apparent.

Figure 15:
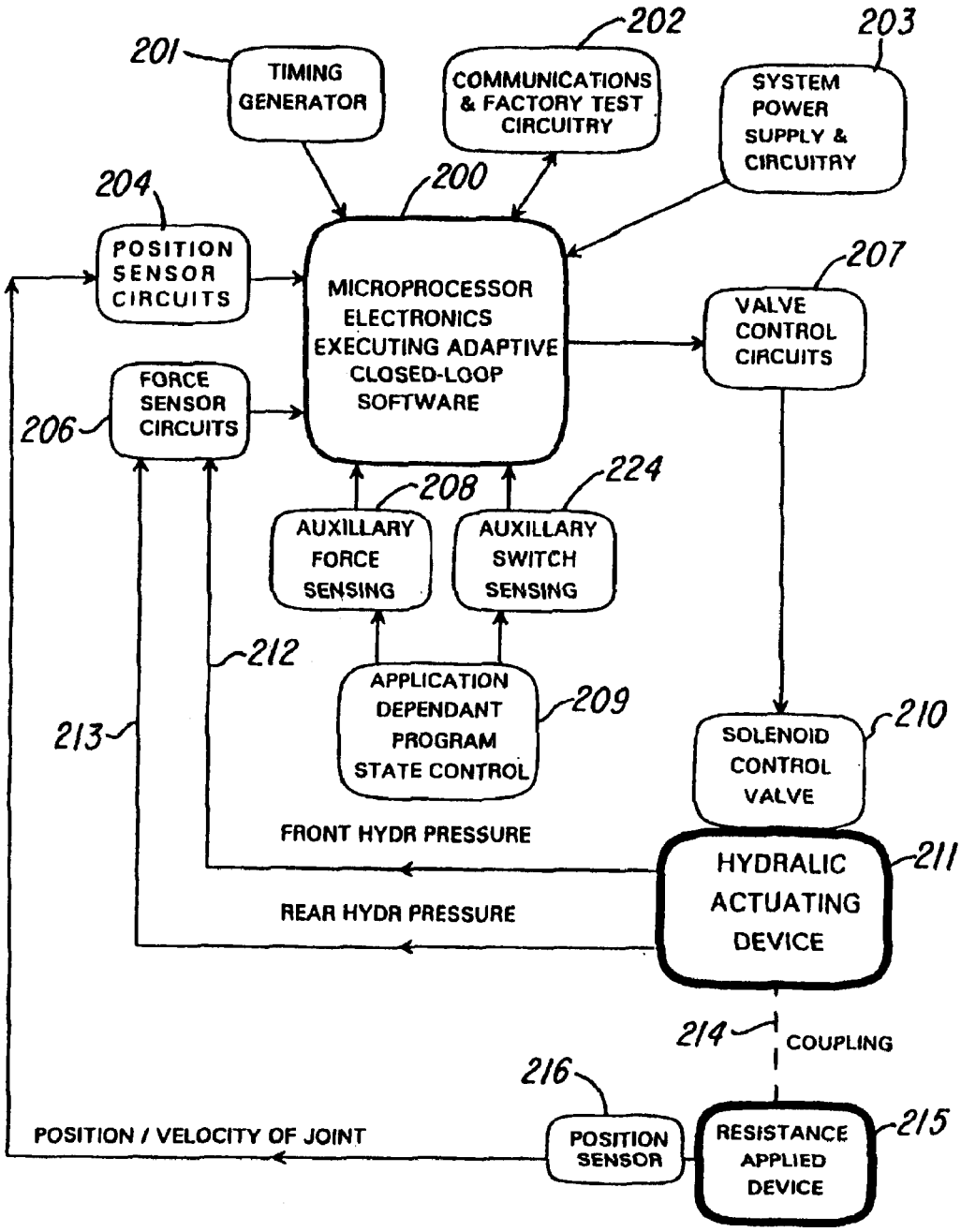
FIG. 15 is an overall block diagram of a computer controlled electromechanical closed-loop resistance device constructed in accordance with the invention.

FIG. 15 shows the overall system control diagram which applies to all the above-mentioned applications. The system is controlled by a conventional microprocessor 200 containing RAM memory, program memory, timers and interrupt control, multi-channel, analog-to-digital converter, and input/output control lines. The microprocessor uses an external clock generated by a timing generator 201. For manufacturing testability of the internal circuitry and for communications with other devices, a system block 202 contains an asynchronous and synchronous serial ports and well as a real-time background mode port.

In all applications of the device, the microprocessor 200 executes its program requiring both sensing and control in a closed-loop manner. The system programs cause a resistance to be applied to the device depending on the sensed position and velocity. Using a hydraulic fluid system, the resistance is applied by a hydraulic actuating device 211 which may be either a rotary vane such as the rotor 20 or a linear movable piston within a cylinder. The resistance is applied by restricting the flow in a closed fluid system by a solenoid control valve 210, such as the valve 32, operated by the microprocessor 200 and its control circuitry 207. The mechanical resistance is applied to a device 215 through a coupler 214. The applied device may be, for example, a knee joint of a prosthesis or a piece of exercise equipment, or a robotics platform which requires restriction in movement and/or velocity.

The position of the applied device is sensed by 216 which may be a potentiometer, proximity detector or a linear hall effect sensor such as the sensor 18. The output of the position sensor is a signal conditioned and scaled by circuitry 204. The analog position signal leaving 204 is converted to digital 8–16 bit number by the microprocessor's A/D converter or an external A/D device for use in the main program. The position is time sampled at fixed intervals. The difference in position between the fixed intervals of time divided by the time sample duration is the velocity of the device movement to be also used by the main program as well as the direction of movement.

To produce the calculated desired resistance to the applied device with consistency and independent of manufacturing tolerances, Fluid viscosity, and/or temperature variations, closed-loop control is used, and the internal fluid pressures 212 and 213 of the rotary or linear hydraulic actuating device 211 is sensed. In a closed hydraulic system, the actuator 211 will produce a high side pressure and a low side pressure on opposite sides of the rotary vane or piston when the control valve is operated to restrict the fluid flow. When the direction is reversed, the high and low side pressures are reversed. The sensed 212 and 213 pressures are signal conditioned and scaled to a usable analog level by circuitry 206. The processed analog hydraulic pressures are converted into a usable digital 8–16 bit valve by the microprocessor 200 or an external A/D converter. In the above mentioned applications, program state control logical branching into different sections of the main program as well as variations in calculations in the application dependent program 209 are accomplished by additional analog force sensors and/or digital switches or buttons 208 and 224 using auxiliary sensing In an exerciser or robotics application, the auxiliary sensing will be a user keypad and/or remote switches. In the knee control prosthesis application, the auxiliary sensing function uses two body weight sensors and two 16 position rotary selector switches.

Figure 16:
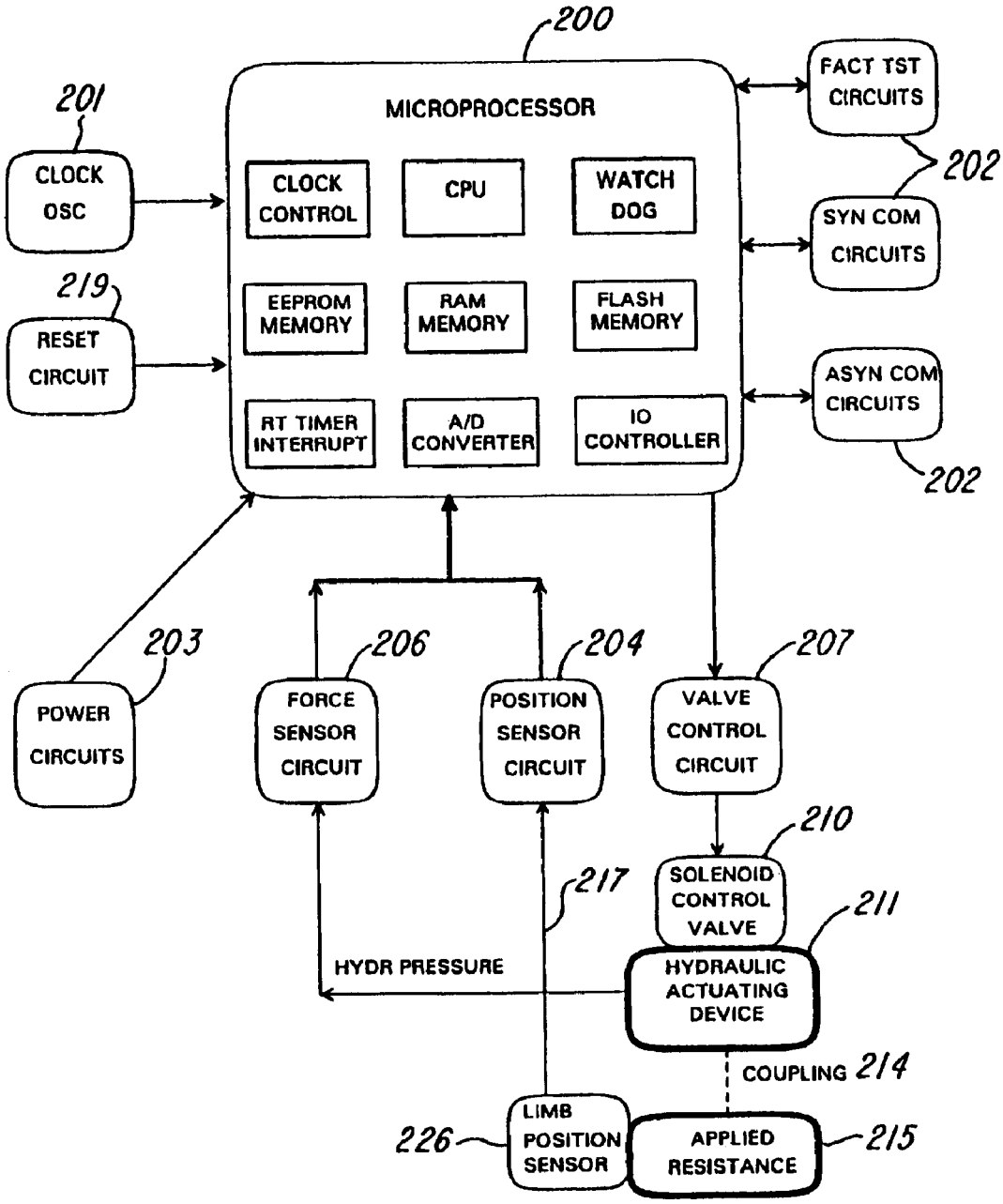
FIG. 16 is a block diagram showing an application of the device for exercise or robotics or damping equipment.
Figure 17:
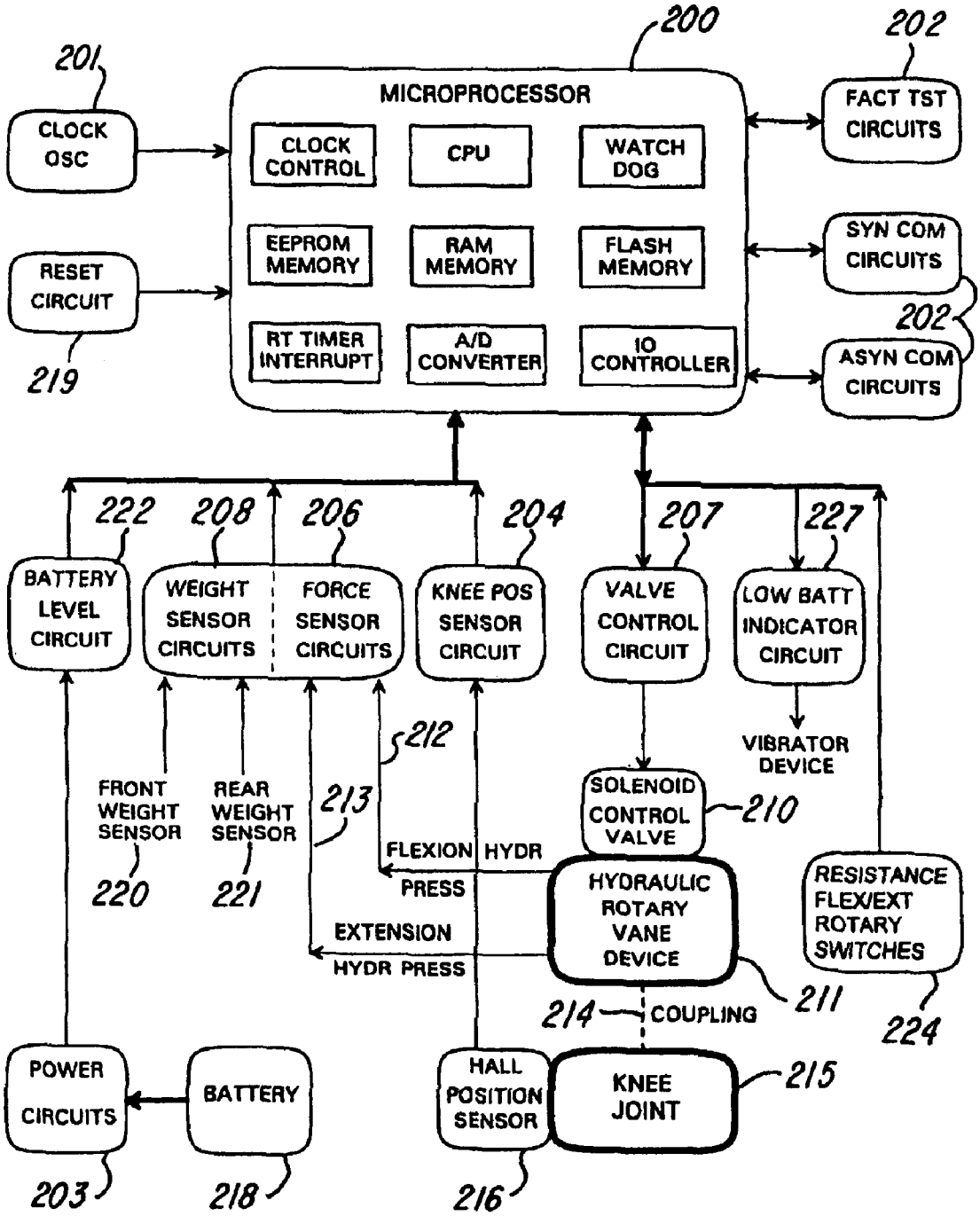
FIG. 17 is a block diagram showing an application of the device for a knee control prosthesis for an amputee.

FIGS. 16 and 17 show the application of the control system of the invention to prosthetic devices, exercise equipment, and robotics. The device of the invention may also be used as a computerized dampening device such as a truck seat shock absorber which would use the FIG. 16 control and component diagram. Due to the fine resolution microprocessor control provided by the invention sensors and hydraulic actuator and control valve, the same type of implemented exercise equipment may be used for medical rehabilitation, programmed to the small steps in applied weight changes as little as 0.1 pound increments to as much as 500 total pounds. The auxiliary input function tells the main program to limit or reduce the loading to the patient if they become distressed from the exercise. The block diagram shown in FIG. 16 is very similar to the overall invention block diagram of FIG. 15 and illustrates the application of the device to exercise equipment, robotics, or a computerized damping device. The application shows a microprocessor 200, communication and test circuits 202, timing generator 201, reset circuitry 219, valve control circuitry 207 and a solenoid control valve 210, position sensor 226 and circuitry 204, hydraulic internal force sensor circuitry 206, and power circuits 203.

FIG. 17 discloses the components for the electronic knee control prosthesis application. The microprocessor 200 executes its application program requiring both sensing and control in a closed-loop manner as described above in connection with FIG. 15. The microprocessor used in this typical application is a Motorola MC68HC912B32 16 bit embedded signal chip processor. This application software being executed on the microprocessor 200 proportionally commands the resistance to be applied to the knee joint of the prosthesis during patient gait cycle using the valve control circuitry 207 to control the proportional solenoid actuated valve 210 or 32. A pulse width modulation technique will also work as well in most applications. The proportional control valve restricts the closed system hydraulic flow generated by the moving knee of the patient, and the rotary hydraulic vane actuator 211 connected by coupling 214 to the knee joint 215. The application software algorithm predicts initially how much control current should be applied to the solenoid valve 210 or 32 given the position, direction, and velocity of the knee joint. The exact resistance error is determined in a closed-loop manner using the sensed high and low side hydraulic pressures 212 and 213 to be conditioned and scaled by circuitry 206 then converted to a digital valve by the microprocessor 200 with respect to the commanded level. The microprocessor inner loop senses the high and low side hydraulic pressures on opposite sides of the rotor 20 and updates the control solenoid applied voltage level at a 1000 times per second rate. The main control loop of the program executes at a rate of 100 times per second.

The knee position sensor 216 is accomplished by a Honeywell linear Hall effect sensor 18 measuring the change in magnetic field with respect to the sensor. The magnet 14 is moved in reference to the sensor 18 or 216 in proportion to the knee angle of the prosthesis. The output of the sensor 216 is conditioned, offset, and scaled by the sensor circuitry 204. The microprocessor 200 converts this 0–5V analog level into an 8 bit digital value. The application program samples the position sensor at a 1000 times per second rate. The application program determines knee direction and course velocity information at that rate. Fine velocity is determined at the 100 times per second control rate. For variances between patients as to their size, weight, and gait characteristics, the prosthenst sets the flexion and extension rotary 16 position auxiliary switches 224. Other auxiliary circuits used for program state control are the two weight force sensors 220 and 221 being modulated, conditioned, demodulated, and scaled by circuitry 206. These weight force sensors are located in the bottom of the prosthesis (FIGS. 5 and 12A–D) to measure the force distribution applied during the gait cycle to determine when toe off, flat footed, and heel strike conditions exist along with their variations. This information is used in the adaptive closed-loop control algorithm with knee position, knee velocity, knee direction, and past gait learned characteristics to control the instantaneous resistance control over varying terrain.

Since this knee prosthesis is worn on the body, the control system is powered by 4 Lithium ion rechargeable batteries 218 or 19 yielding 14.4 volts. Power is split off into two circuit applied voltages being 7.2 volts for the system logic supply and raw 14.4 volts for the proportional control solenoid drive circuits. The raw voltage is monitored to detect a low battery condition by circuit 222 which scales the battery voltage into a 0–5 volt level to be read by the microprocessor 200 using its A/D converter. The microprocessor and associated logic circuits require 5V which is regulated from the 7.2 voltage input by the power circuits 203 which include a conventional low dropout three pin regulator integrated circuit. The Lithium ion batteries are recharged in a two hour period and then switched into a trickle charge mode by a LM3420-16.8 integrated circuit produced by National Semiconductor.

Figure 18:
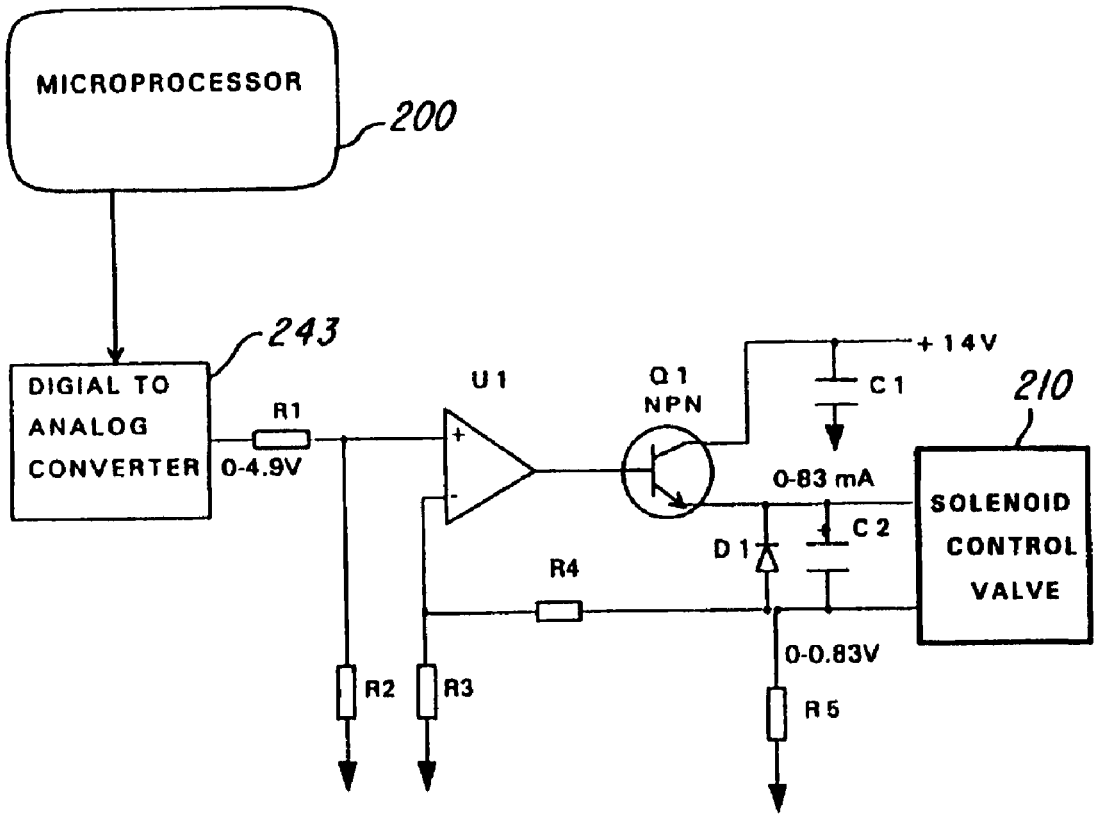
FIG. 18 is a circuit diagram of the electronics for controlling the solenoid control valve in the resistance device.

FIG. 18 illustrates the circuitry 207 for the solenoid control valve drive 210 or 32. The proportional solenoid control valve requires very low power of only a maximum of 1 watt. The drive to the solenoid is a constant current type over a range of 0 to 83 milliamps. The resolution in this application of the 0 to 83 milliamp level is 1 part in 255 or 0.325 milliamps per step using the 8 bit digital potentiometer 243. This AD8400AR10 is an integrated circuit produced by Analog Devices. The microprocessor 200 updates the device level at a 1000 times per second rate. The reference to the digital potentiometer is the 5 volt logic supply. As the level is adjusted in the 256 levels, the output of the wiper will change from 0 to 4.9 volts. The voltage signal is converted into a constant current drive by the operational amplifier U1, transistor Q1, and three resisters R1, R2, R3, R4, and R5. The output of the digital potentiometer seen by a differential input operational amplifier with a gain of 0.169 as seen by resisters R1, R2, R3, and R4. NPN transistor Q1 is used as a current amplifier in an emitter follower mode. Diode D1 is used in the circuit to eliminate the reverse EMF effects of the solenoid control valve coil. Electrolytic capacitor C2 is used as part of a low pass filter with the solenoid coil to reduce the high frequency bandwidth of the circuit. C1 is used as a high frequency power supply bypass.

As the voltage from the digital pot is increased, the circuit applies a voltage across the solenoid coil. The current through the coil is in series with the sense resister 10 ohm R5. This constant current circuit increases or decreases the operational amplifiers output voltage until the voltage seen at the top of the sense resister is equal to the commanded voltage. Thus to require a 0 to 83 milliamp drive to the solenoid coil, a 0 to 4.9 volt input is required. The constant current circuit automatically compensates for coil resistance manufacturing variations and temperature effects.

Figure 19:
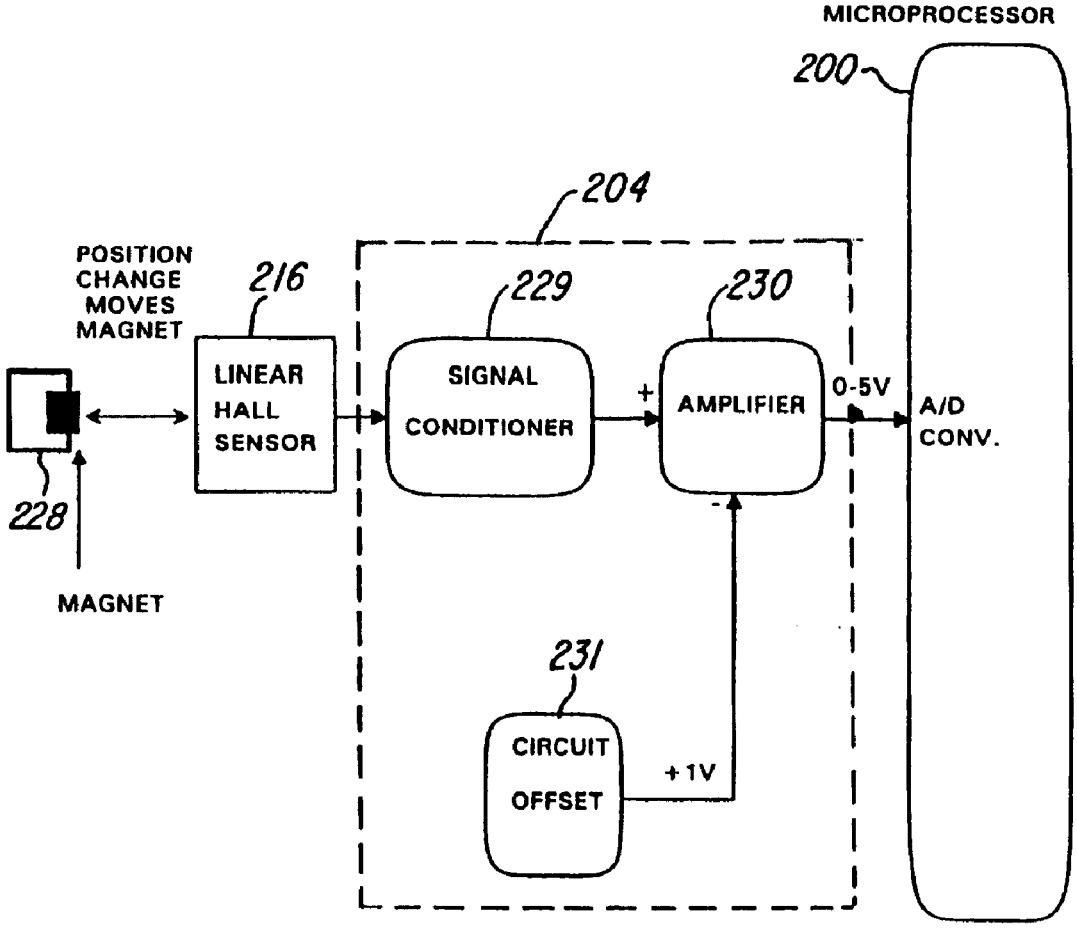
FIG. 19 is a circuit diagram for the Hall position sensor electronics in the resistance device.

Referring to FIG. 19, the circuitry for the linear Hall effect position sensor 216 or 18 is signal conditioned, offset, and amplified by the knee position circuitry 204. A magnet 228 or 14 is mounted on the lever arm 12 which is pivoted by a cam surface on the retainer plate 8 so that the lever arm 12 moves directly proportional to the knee angle. As the magnet 14 moves towards or away from the sensor 18, the Honeywell SS94A1B sensor 216 or 18 varies its output voltage depending on the north or south pole magnetic field. The sensor 18 outputs a 2.5 volt signal depending on the amplitude of the magnetic field and the magnet polarity. In this application, the polarity of the magnet is such that decreasing the distance until the magnet touches the sensor yields 0 volts, and totally removing the magnet from the sensor yields an output of 2.5 volts. The minimum distance at zero degrees knee extension if 0.10 inches yielding a minimum voltage of 1 volt. In FIG. 19, block 229 buffers and low pass filters the 1 to 2.5 volt hall position signal at a 100 Hz corner frequency to remove any high frequency components. The second stage operational amplifier 230 increases the signal level by 3.33 times as well as removing the offset of 1 volt from reference 231 to yield an output level of 0 to 5 volts.

This analog output is then converted into a digital output for use by the main program by the microprocessor 200.

Figure 12A:
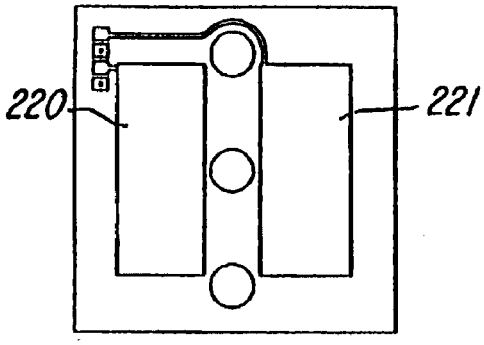
FIGS. 12A–12D are views of a capacitance force sensor used in the knee control unit.
Figure 12B:
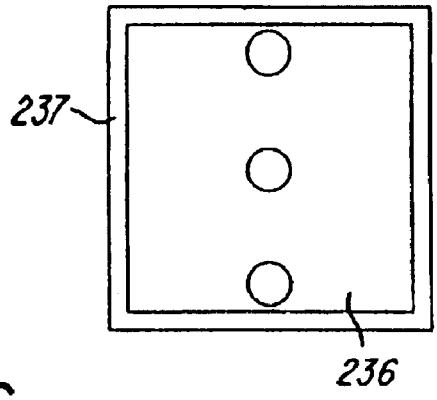
Figure 12C:
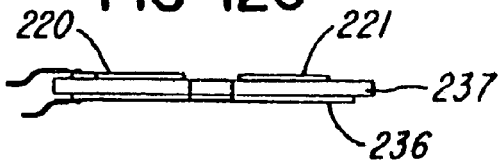
Figure 12D:
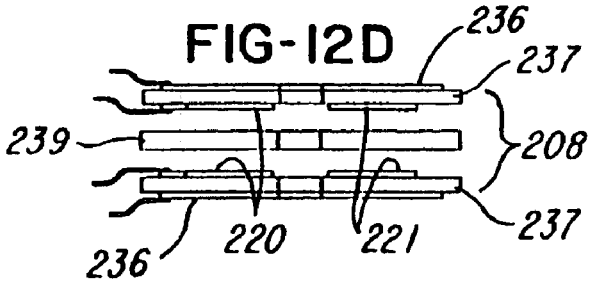
Figure 20:
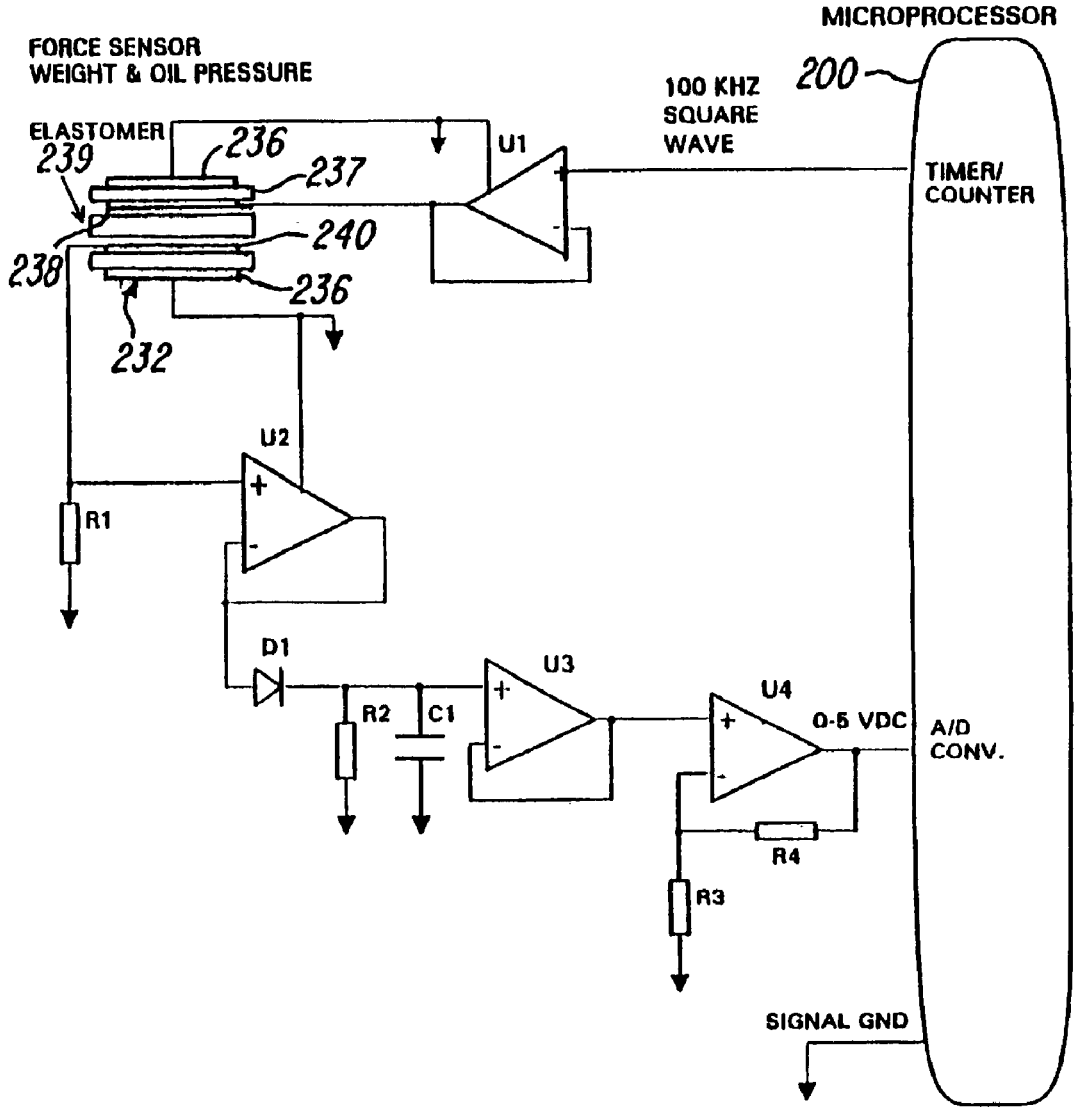
FIG. 20 is a circuit diagram for the force sensors for the knee control unit.

FIG. 20 illustrates the force sensor 232 or 68 and its associated circuitry. As shown in FIG. 17, the weight sensor circuitry 206 is used for closed-loop control of the solenoid proportional control valve 210 or 32. The weight force sensor 200 and 221 (FIG. 12A) and weight sensor circuitry 206 are used for program state control. The circuitry design is identical except for the final amplification gain of U4, R3, and R4 in FIG. 20. This is an improved version of a capacitance sensor. FIGS. 12A & B show the actual sensors 220 and 221 used in the knee control application. The enhanced sensor 232 (FIG. 12D) is constructed of two double sided printed circuit cards and an elastomer separator. As force is applied to squeeze the plates together, the signal applied on the side of the elastomer is coupled proportionally to the plate on the other side. Thus as the force is increased, the reference signal level transferred to the second plate is intensified by the increase in capacitance between the plates. The amount of force that can be measured by the sensor is a function of the elastomer density used and the gain of the demodulating circuitry. The stiffer the elastomer, the more force can be applied before fully compressing the plates together. Too much stiffness in the elastomer reduces the dynamic range of the sensor. The elastomer having a particular durometer is selected from each application.

In FIG. 20, the sensor application uses the microprocessor 200 to generate a 100 kHz square wave reference signal. This signal is buffered by operational amplifier U1. The emitter side of the enhanced capacitance sensor is constructed on a double sided printed circuit card. A conductive reflector 236 is on the outside and a conductive reference pad 238 is on the other. The insulated printed circuit card 237 is made of glass epoxy. The reference 100 kHz signal is coupled across the elastomer 239 to the receiver plate 240 on another card 237 and which is protected from outside emissions by another shield plate 236. The received coupled 100 kHz signal is proportional to the compression of the plates and is developed across resistor R1. The signal is then buffered by operational amplifier U2. The received signal is converted into a proportional DC level by the RMS converter circuit consisting of D1, R2, C1 and operational amplifier U3. The DC level is scaled into a 5 volt maximum level by operational amplifier U4, R3 and R4. The microprocessor 200 converts this analog signal into a usable digital valve by its onboard analog-to-digital converter.

Figure 11A:
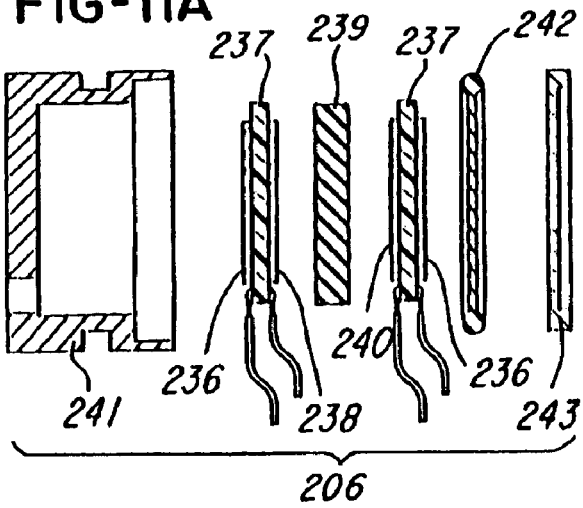
FIG. 11A is an exploded view in section of the capacitance pressure sensor shown in FIG. 8.
Figure 11B:
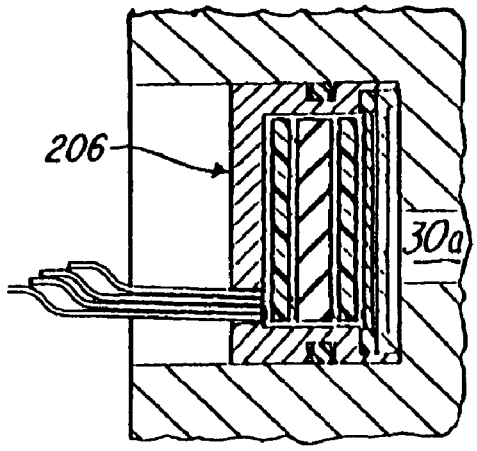
FIG. 11B is an axial section of the assembled sensor.

In the knee control application (FIG. 17), two configurations of this sensor technology are illustrated. These are the hydraulic oil pressure sensors 206 and the body weight sensors 208. FIGS. 11A & B show one of the two oil pressure sensors 206 or 31 or 34 used for closed-loop control of the solenoid control valve proportional positioning. Oil ports 30a and 30b within the housing 15 have pressure communication with the chambers 25 and 26 on opposite sides of the hydraulic vane rotor 20. Internal pressure changes is transmitted to each sensor 206 by end cap 243 (FIGS. 11A & 11B) and diaphragm 242. The diaphragm pressure compresses the reference printed circuit card 237 containing the reference plate 240 and reflector plate 236 against the elastomer 239. The signal is coupled to the receiver plate 238 and shield plate 236 on another circuit card 237. The assembly is housed by the sensor enclosure cup 241 and with its associated circuitry operates as described above.

Referring to FIGS. 12A–D, the body weight force sensor 208 or 68 of the knee control application is constructed of two 2" by 2" double sided printed circuit boards 237 being separated by a sheet of elastomer 239. The capacitive plates 220 and 221 are 0.5" by 1.25", and two reference plates and receiver plates 238 and 240 are used to produce a weight distribution sensor 68. This sensor 208 or 68 is located in the base of the knee control. From the compression in the forward, middle, or aft force distributions, the system software can determine toe off, flat footed, or heel strike for program state control. This assembly with its associated circuitry also operates as described above.

In the knee control application (FIG. 17), the system software is written in assembly code for a Motorola MC68HC912B32 microprocessor 200. This microprocessor 200 includes a 16 bit CPU, an interrupt controller, an 8 channel 8 bit A/D converter, 1 kilobyte of RAM, 32 kilobytes of flash EPROM program memory, 756 bytes of EEPROM, one real-time timer interrupt, six timer-counters, a watchdog circuit, and a complex of communication devices for interacting with other systems such as a RS-232 serial peripheral, a synchronous serial peripheral, a BDLC synchronous serial peripheral, and a real-time background mode interface.

The knee control software application includes subroutines which are common to robotics and exercise devices. Referring to the general block diagram of FIG. 15, the microprocessor 200 outputs to a valve control circuit 207 to operate the proportional solenoid control valve 210, such as the valve 32, which in turn applies resistance by restricting the fluid actuating device 211, such as the rotor 20. Two pressure sensors 212 and 213, such as the sensors 31 and 34, are read by the microprocessor 200 to be used in its closed-loop control of the valve to maintain correct applied force to the device coupled to the actuator regardless of manufacturing tolerances, temperature variations and fluid viscosities. The pressure sensors measure the differential pressure across the actuator regardless of the actuator direction of movement. The device 215 upon which the resistance is applied, contains a position sensor 216, such as the sensor 18, which allows the system software to close the outer control loop as to determining the device's position, velocity, acceleration, and direction of movement. In most cases, the system software also uses auxiliary analog circuitry 208 and switch inputs 224 for program state control.

Referring to the knee control application software discussed above in connection with FIG. 17, the system software being executed on the microprocessor 200 outputs the required 8 bit control valve level of the valve control circuitry 207. The digital potentiometer uses three I/O pins on the microprocessor. The software low level driver routine synthesizes the required synchronous serial 10 bit interface which sets the required 0–4.9 volt input drive to the constant current valve control amplifier. The fluid pressure force sensors 212 and 213, such as sensors 31 and 34, are analog processed and scaled by the fluid pressure sensor circuitry 208. The demodulated 0–5 volts proportional signal is read by the microprocessor 200 using the A/D fluid sensor low level drive routine. All the fluid pressure and weight sensors use a 100 kHz reference square wave signal generated by the microprocessor onboard counter-timers and initialized in the software power-on reset routine. This signal is buffered by the hardware and sent to the sensors.

The outer control loop feedback is obtained by the linear hall effect position sensor 216, such as the sensor 18, attached to the moveable knee joint housing 15. The analog output of the hall effect sensor 18 is non-linear. Part of the linearization is accomplished by the cam surface on the retainer plate 8 (FIG. 6). The majority of the position interpretation is accomplished by a software lookup table driver routine which converts raw position into actual knee angle in degrees and tenths. The raw position information is scaled and offset by the position sensor circuit 204 which is read by the microprocessor 200 using the A/D position driver software routine.

Two types of auxiliary program decision state control functions are used. One being analog and the other being digital. The analog program state sensors 220 and 221 form the dual body weight sensor 68 attached to the bottom on the knee control frame 5. The sensors 220 and 221 sense the amputee's weight being applied to the toe or flat footed, or heel force to aid the main software program control. The two sensors 220 and 221 also use the 100 kHz reference signal. The demodulated and scaled resultant analog signals are ready by the microprocessor 200 by A/D software drivers. Variations between the amputee's size, weight, age, strength are accommodated by the setting of ten levels of flexion and ten levels of extension profiles. These settings are made by the prosthetist during the knee control fitting. The main subminiature printed circuit card contains two sixteen position miniature rotary digital hexadecimal switches. The first ten positions are used for the prosthetic adjustments of flexion and extension and the other six are for special modes of operation tailored for sports and geriatrics. The two 4 bit auxiliary switch inputs 224 are read directly by the microprocessor using the switch software driver input routine and the I/O input pins and associated internal pull-up resisters. The input signals are normally seen as a digital high TTL level except when grounded by the switch.

Since this knee control application is battery powered, additional software low level drivers are required for this application. The battery pack 218, such as the battery pack 19, are conditioned and split into 5, 7.2, and 14.4 volts by the power circuits 203. The battery level is monitored by the microprocessor 200 through the conditioned battery sensed signal 222. The analog 0–5 volt filtered level is read by the microprocessor 200 by the low level software A/D battery driver routine. If the programs determine that the battery is within 30 minutes of a minimum safe level of operation, the two safety software routines will be activated to cause a vibrator circuit 227 to produce an alert to give the user impending notice of shutdown. The communication to the outside world to/from the knee control is through the microprocessor's internal communication ports and interface hardware circuitry 202. The asynchronous (SCI) and synchronous (SPI) serial data ports are used for special clinical data capture and control. The background mode (BDM) port is used for the factory test interface during the manufacturing process as well as during software development. The main programming of the 32 kilobytes flash memory is programmed through the BDM port.

Figure 22:
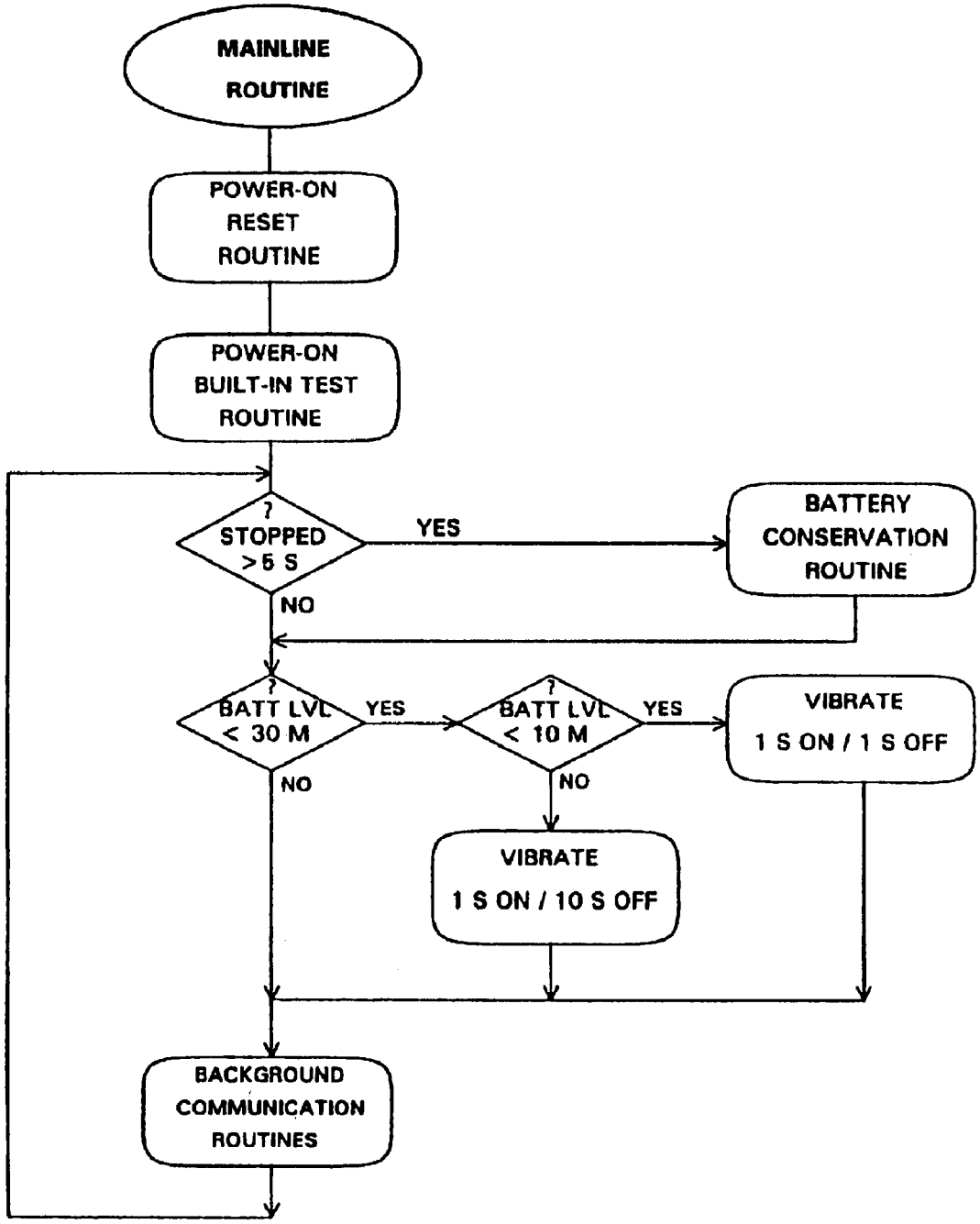
FIG. 22 is a mainline software routine block diagram for the knee control unit.

FIG. 22, shows the knee control mainline software subroutine. When the microprocessor 200 is energized, the microprocessor will be vectored to the RESET subroutine. This routine initializes the programmable data ports and peripherals, to the desired analog and digital level such as the two weight sensors and the two fluid pressure sensors needing their 100 kHz reference for correct operation. The proportional control valve drive level is set to zero until required to change by the application program. When the system is initialized, a system built-in test program is entered to determine if the knee control electronics are working according to the factory specification. If not, the system vibrator will be activated ½ second on and one second off to alert the user that the system has seen a failure and it is unsafe to use. Until the failure is corrected, normal system application execution will be disabled. During normal operation, the system control and mode determination is accomplished by the two interrupt routines occurring at a rate of 100 and 1000 times per second.

The mainline program checks for low battery conditions and outside communications in the system idle time when not executing the interrupt driven adaptive closed-loop time dependent application. The mainline program examines two low level battery conditions; one being if the level is below 30 minutes of safe operation and the other if the battery is below 10 minutes of safe operating time left. The user is informed of the immediate loss of the system use from a low battery condition by either a vibration of one second on and 10 seconds off for the 30 minute case or one second on and one second off for the 10 minute case. In normal use, the Lithium Ion battery pack will last 22–30 hours before needing to be recharged. The knee control prosthetic will normally be recharged by the user every night. If needed, the user can charge the battery pack to 90 percent of its level in two hours while at work.

Figure 23:
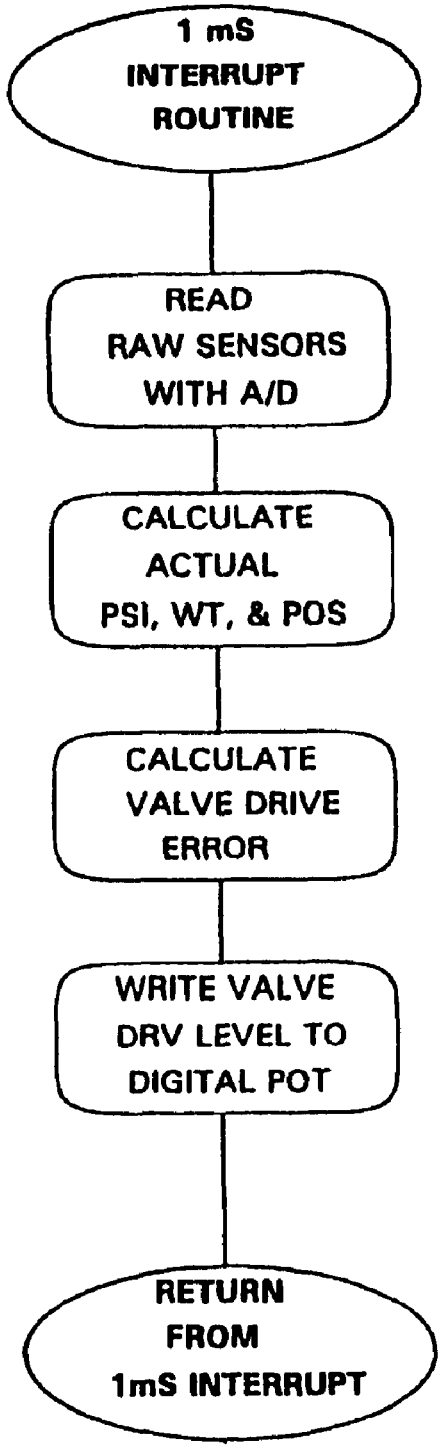
FIG. 23 is a block diagram for the one millisecond interrupt software routine for the knee control unit.

FIG. 23 shows the one millisecond software interrupt routine for the knee control unit. This routine captures the raw sensor data and updates the valve control at a 1000 times per second rate. The raw sensor data is read by the individual A/D channels. These 8 bit valves are converted into actual scaled fluid pressures in psi, amputee forward and aft weight distributions in pounds, and knee angle in degrees by the low level software drive routines using lookup conversion tables and numeric calculations. The valve is also controlled in a closed-loop manner at this 1000 times per second rate by calculating a new control level to be written to the control solenoid valve electronic circuit. A calculation is made of the error difference between the required force and the sensed hydraulic fluid pressure. This difference is used in a non-linear gain equation and lookup table to determine the next best guess at the valve level control to meet the desired instantaneous resistance with the least error or delay. The drive byte value obtained by written to the digital potentiometer by the low level driver software routine converting the byte into the required 10 bit serial data as well as controlling the clock and enable bits on a bit-by-bit manner.

Figure 24A:
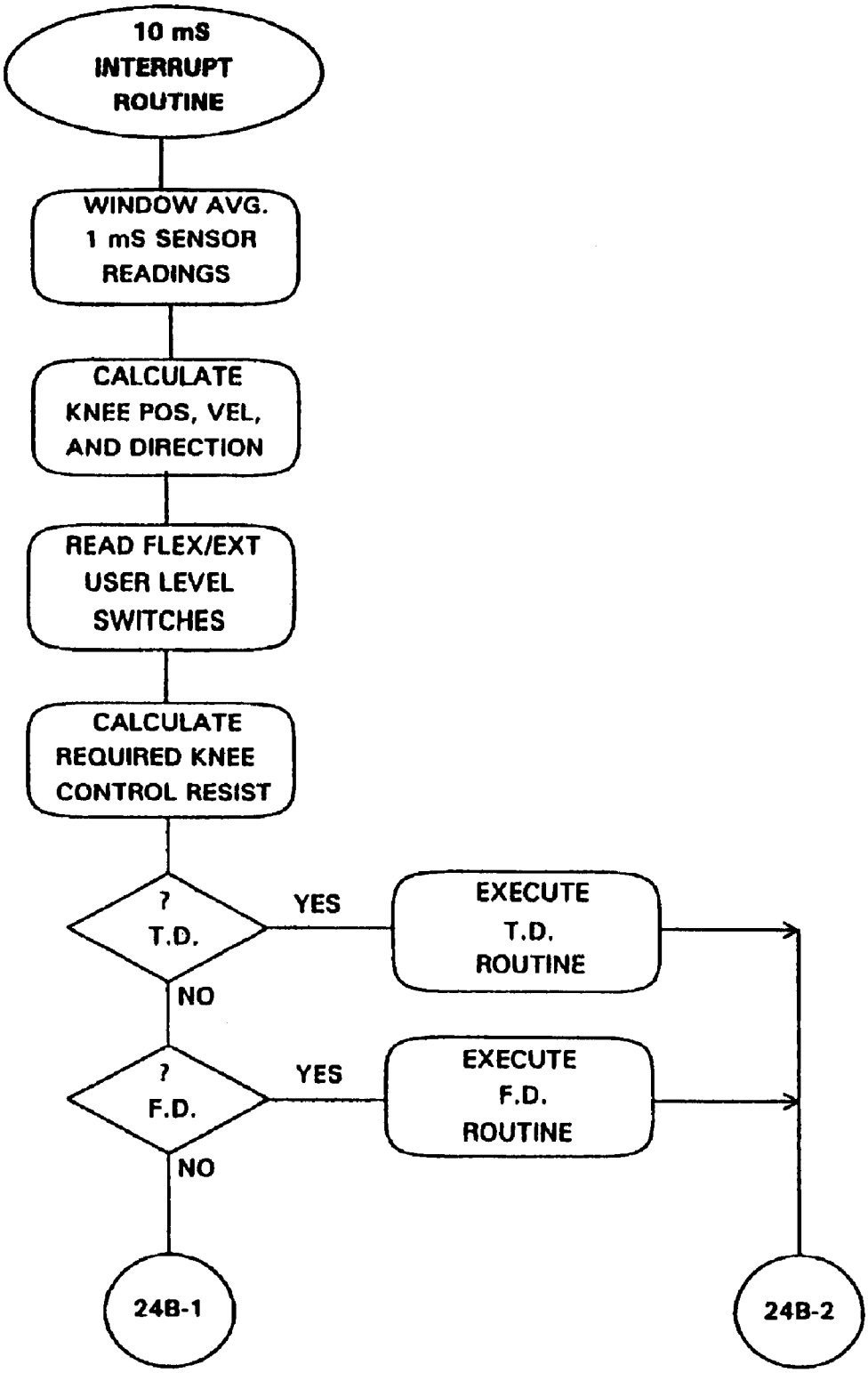
FIGS. 24A & 24B show the block diagram for the ten millisecond software routine for the knee control unit.
Figure 24B:
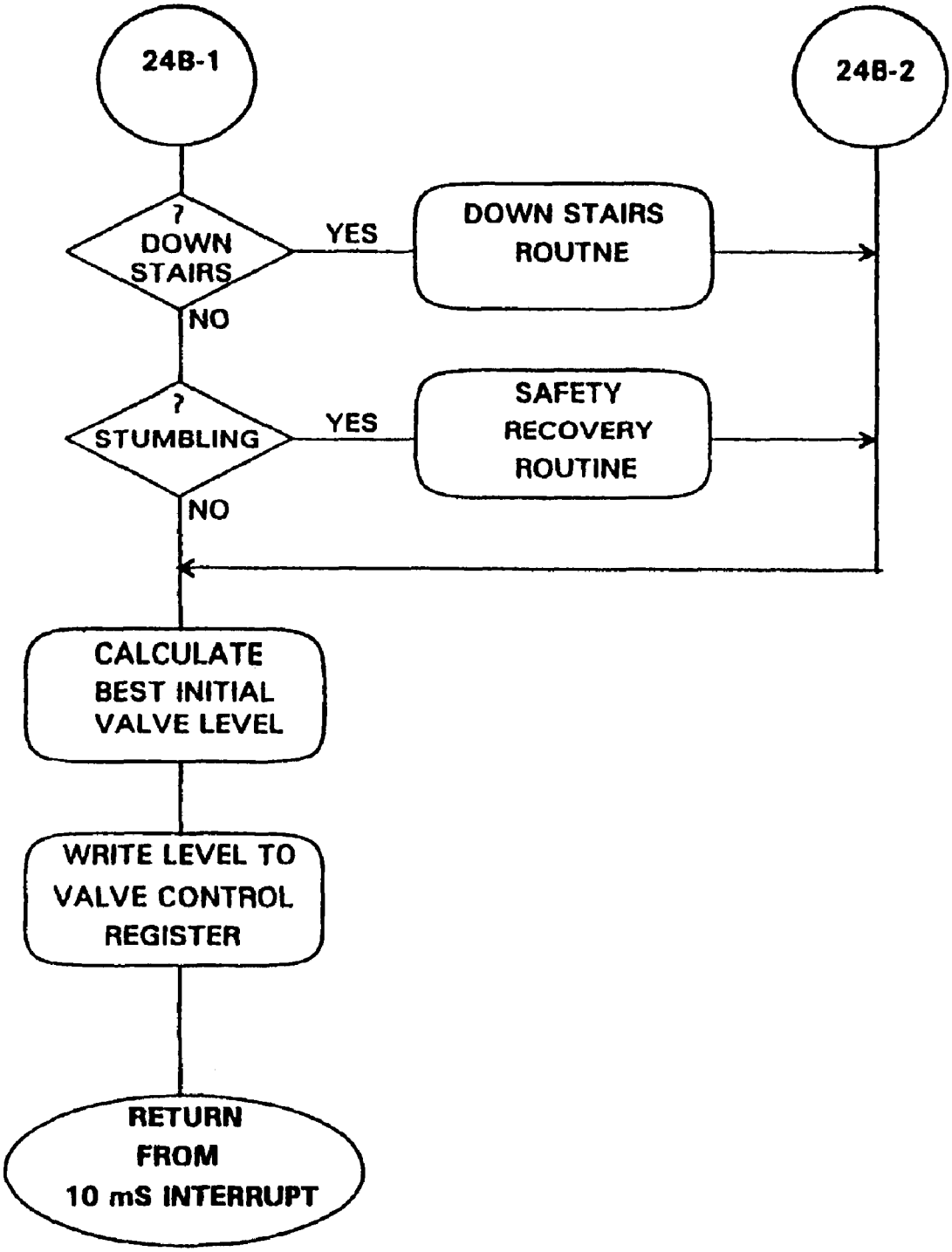

Referring to FIGS. 24A and 24B, the knee control unit has a ten millisecond interrupt routine which is the main control loop where the majority of the calculations and program control are accomplished. This routine executes at a rate of 100 times per second. The software application requires knee position, knee velocity, knee direction, extension and flexion patient switch settings, and forward and aft body weight distribution. The position sensing is the most important parameter. To obtain smooth and accurate position information, the ten 1 millisecond interrupt position samples are stored in an array. These ordered samples are time weighted window averaged to obtain the system knee position used. The previous old position is subtracted from the new position and divided by 10 milliseconds to yield a short term knee velocity.

The new position is also subtracted from an old position of 50 milliseconds ago and divided by 50 milliseconds to calculate a long term knee velocity. The short term knee velocity is used for the determination of knee direction. The long term knee velocity is used for the determination of the knee resistance to be applied. The knee applied resistance calculations are based on the mathematical transfer function of a non-electronic hydraulic knee control obtained through extensive engineering characterization. A set of tables and equations are used to calculate the requires applied resistance in terms of PSI for any instantaneous knee position, knee velocity, knee direction, and flexion or extension patient switch setting. When the normal swing phase calculations are completed, the normal swing phase resistance is stored in the RAM for later use.

The program flow then determines if additional modes of operation are to be executed. The first decision path is Terminal Deceleration (T.D.). When the prosthetic knee is approaching full extension, the system software will apply an additional high resistance at less than 10 degrees to stop the knee hyper extending. Likewise, another routine is used for slowing the prosthetic knee during flexion. This is called Flexion Deceleration (F.D.). This routine is used to keep the knee from flexing too far. The F.D. routine will increase resistance proportionally past 65 degrees flexion and completely stops the knee control at 70 degrees. Other auxiliary modes include the determination of walking down stairs and the determination of stumbling. The down stairs mode is determined by knee angle and weight distribution as seen by the two weight force sensors 220 and 221. The electronic control extends the decaying stance mode of the mechanical portion of the control. If stumble recovery is required, it applies a high resistance to the knee control for a period of time and then delays it to zero. This mode attempts to protect the patient from falling and is detected by knee velocity, knee angle, and weight force distribution.

When the resistance software flow is complete, the desired force level to be applied is stored in a RAM variable. The application software will compute the best valve control level based on the knee velocity, knee direction, hydraulic characteristics, and valve characteristics. This level is written to a RAM variable location for use by the 1 millisecond interrupt routine previously mentioned.

Figure 21:
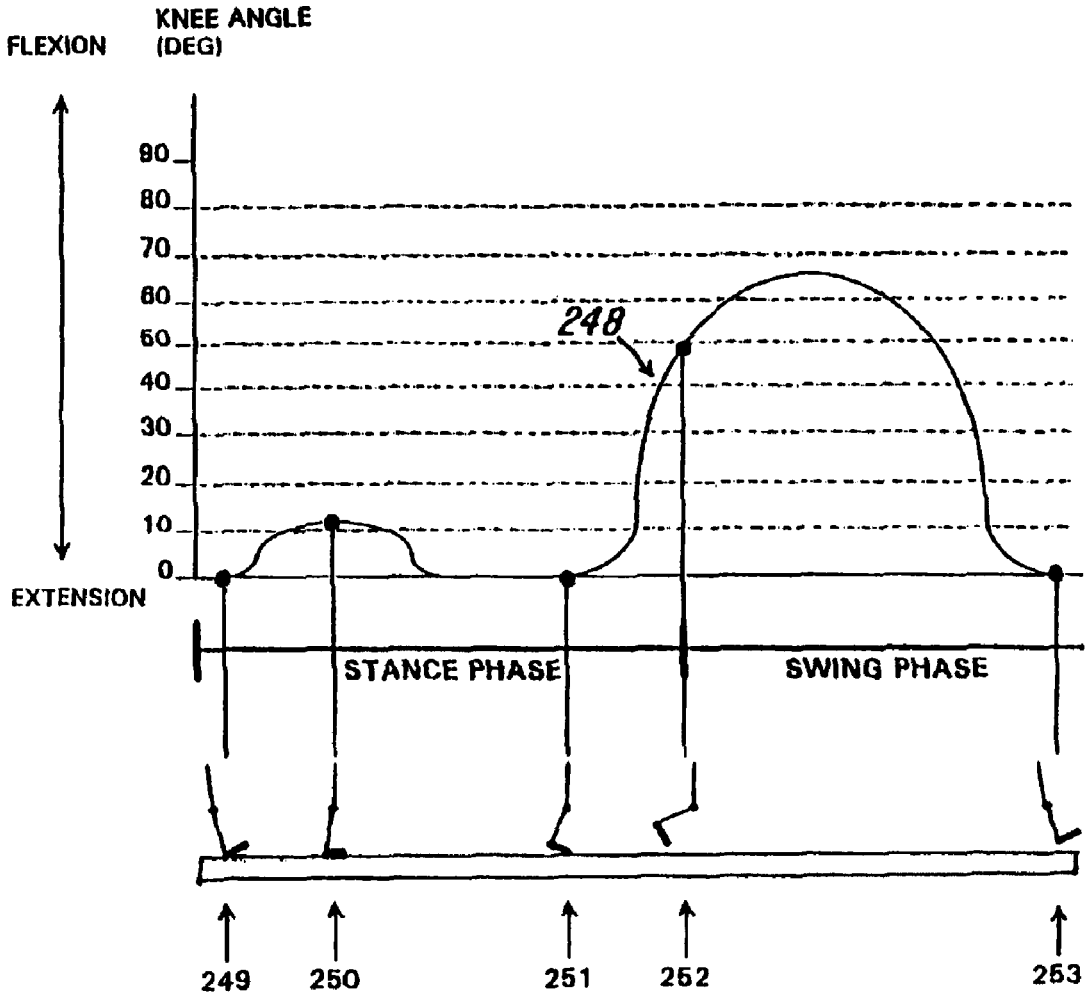
FIG. 21 is a gait knee angle diagram for the knee control unit.

The knee control application gait summary is shown in FIG. 21. The gait knee angle is shown by the curve 248. The swing phase is active when the knee control is off the ground with the knee bending in flexion or extension. Swing phase starts at toe off position 252 and is completed by the time the heel is just ready to strike at position 253. The electronic control is active anytime the knee is at any angle greater than zero except when it detects that the knee has stopped for more than 5 seconds. The stance phase consists of a heel strike position 249, full weight bearing load position 250, and almost toe off but still touching ground position 251.

Figure 25A:
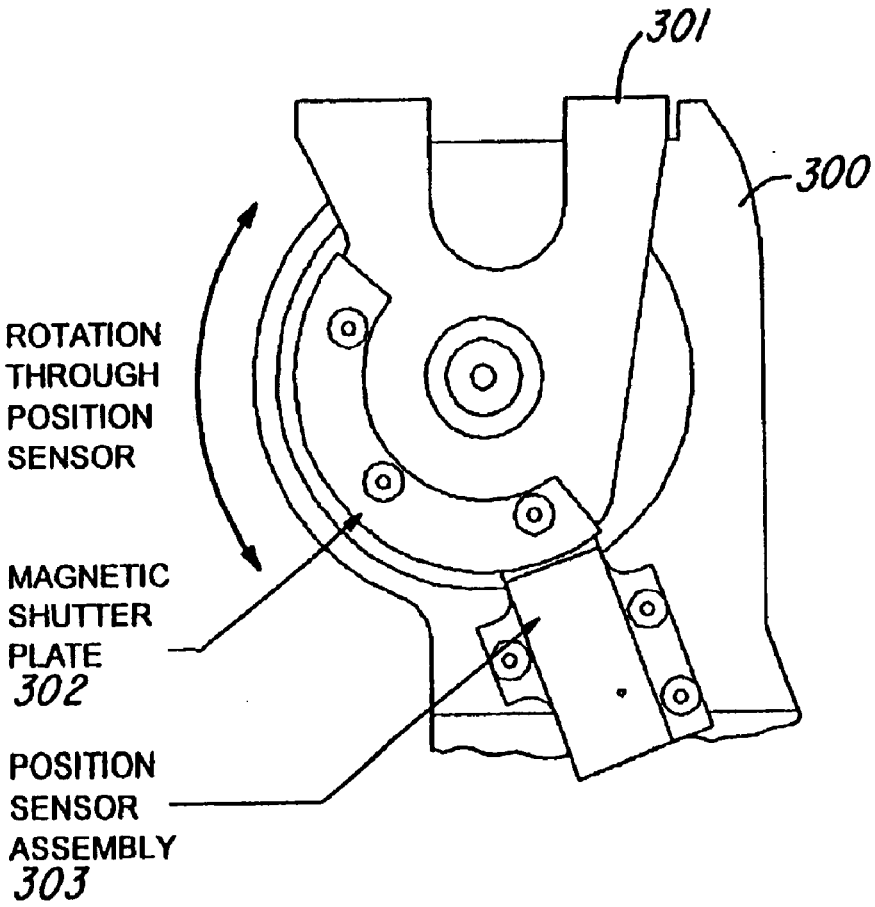
FIGS. 25A & 25B illustrate diagrammatically a magnetic shutter position sensor assembly constructed in accordance with a modification of the invention and its use on a knee control unit.
Figure 25B:
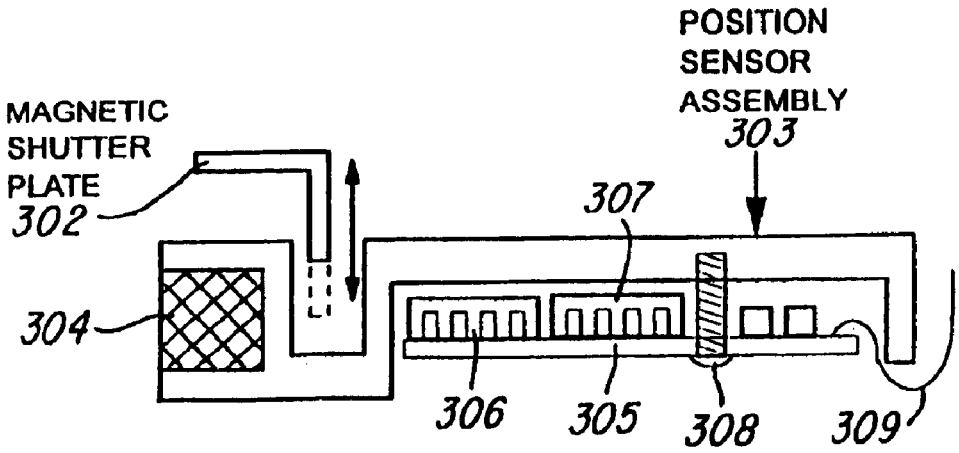

FIGS. 25A–31 show an alternate electronically controlled proportional servo valve and magnetic sensors for knee position, oil pressure and weight bearing. The knee position sensor is shown in FIGS. 25A & 25B and measures the absolute knee angle between the housing of a hydraulic actuator 300 and a knee plate 301 attached to the patient's socket, by sensing changes in a fixed magnetic field with a magnetic sensor assembly 303. The changes in the magnetic field are caused by the movement of an arcuate magnetic shutter plate 302 mounted on the knee plate 301.

The magnetic position sensor assembly 303 consists of a sensor housing enclosing a high output permanent magnet 304 (FIG. 25B) and defining a flux air gap which receives a tapered wail of the shutter plate 302. A magnetic sensor electronic printer circuit card 305 is secured to the housing by a screw 308. The sensor electronics measure the amplitude of the magnetic field as generated by the high output permanent magnet 304 and sensed through the air gap. The sensing of the magnetic field is accomplished by a GMR sensor IC 306, and the signal is conditioned by an instrumentation amplifier 307. The signal level is transmitted to a microprocessor controller card by a cable assembly 309 for further signal conditioning and conversion to a usable digital value for use in the closed-loop control. The curved wall of the magnetic shutter plate 302 is tapered along its length for causing a disturbance or variation of the fixed magnetic field by moving the magnetically conductive material of the shutter plate into and out of the air gap between the magnet 304 and the GMR IC sensor 306 in response to relative rotation between the plate 302 and the actuator 300.

Figure 31:
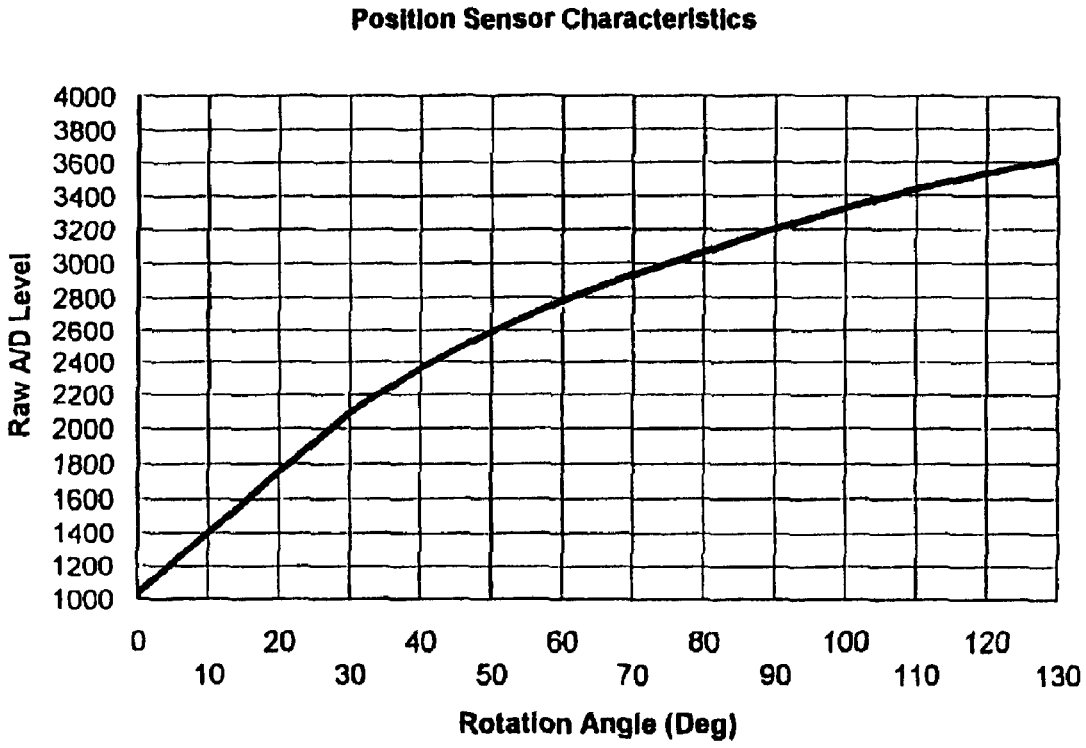
FIG. 31 is a chart showing the nonlinear characteristic curve for the magnetic shutter GMR sensor of FIG. 25B.

The magnetic shutter position sensor assembly 303 generates a nonlinear output which is shown by the chart of FIG. 31. Through a software algorithm, the curve is divided into 13 equations representing 10 degrees of movement each which can be approximated by a series of straight line equations. This approach requires significantly less memory than a 12 bit 8192 byte lookup table which would require 25% of the imbedded microprocessor's program memory capacity. The sensor is calibrated by measuring the magnetic levels every 10 degrees over 0–130 degrees, the correct equation coefficients and stores these in the microcontroller's nonvolatile electrically erasable memory for use by the main executable application program.

Figure 26:
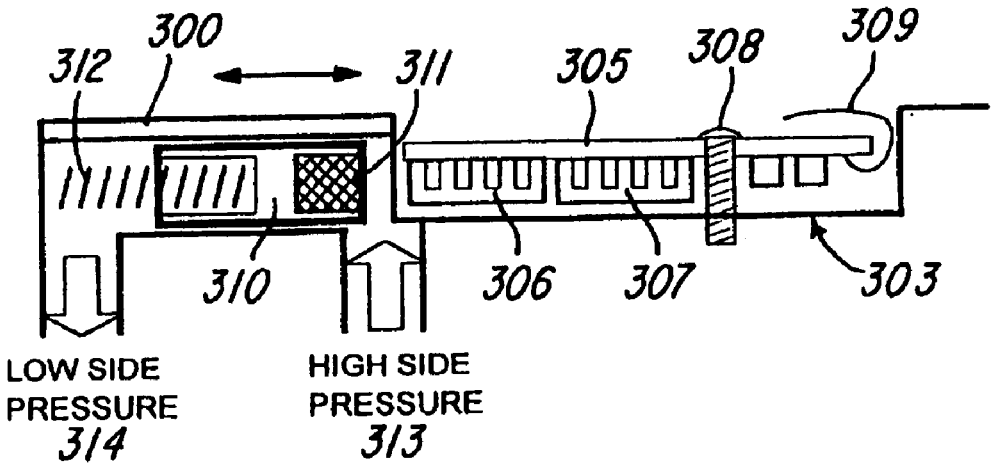
FIG. 26 illustrates diagrammatically a magnetic fluid pressure sensor assembly constructed in accordance with a modification of the invention.

FIG. 26 shows an alternate pressure sensor embodiment comprising a GMR magnetic differential fluid or oil pressure sensor. This sensor is contained in the main hydraulic actuator housing 300. The high side hydraulic pressure 313 is applied to one end of a movable piston 310 containing a high output magnet 311, while the low side oil pressure 314 is applied to the opposite end of the piston. The hydraulic force being applied to the high pressure end of the piston pushes against a bias spring 312 having a sufficient spring constant to allow the piston to move about 0.050 inch with 500 PSI applied differentially. The maximum movement of the piston is about 0.100 inch.

The actuator housing 300 is constructed of aluminum and is sealed from leakage of the hydraulic fluid to the environment. The sensor electronic assembly 303 is similar to the position sensor electronic assembly 303 described above in reference to FIG. 25B and is mounted in a cavity outside of the sealed housing for sensing the internal magnetic field of the magnet 311 through the aluminum housing. The sensor card 305 is mounted on the housing with a screw 308. At zero hydraulic pressure, the air gap between the magnet and the GMR IC bridge sensor 306 is about 0.195 inch but increases to about 0.245 inch at 500 PSI differential pressure. As mentioned above, the common sensor card electronics contain the instrumentation amplifier 307 for signal conditioning. The signal level is transmitted to the microprocessor controller card using the cable assembly 309 for further signal conditioning and being converted to a usable digital value for use in the closed-loop control of the hydraulically applied resistance to the knee.

A patient weight bearing sensor mechanism (FIG. 27) is accomplished in a similar manner. In two different forms of this mechanism, one or two weight sensors may be used. If mechanical weight being stance is used, then only one weight bearing sensor is required to assist the mechanical stance and is used in a stumble recovery mode. If the application requires a smaller size system with less of a mechanical fail safe, a full electronic weight bearing stance is implemented using two weight sensors indicating heal and toe applied forces. Regardless, the one or two sensor application operate in a similar manner.

Figure 27:
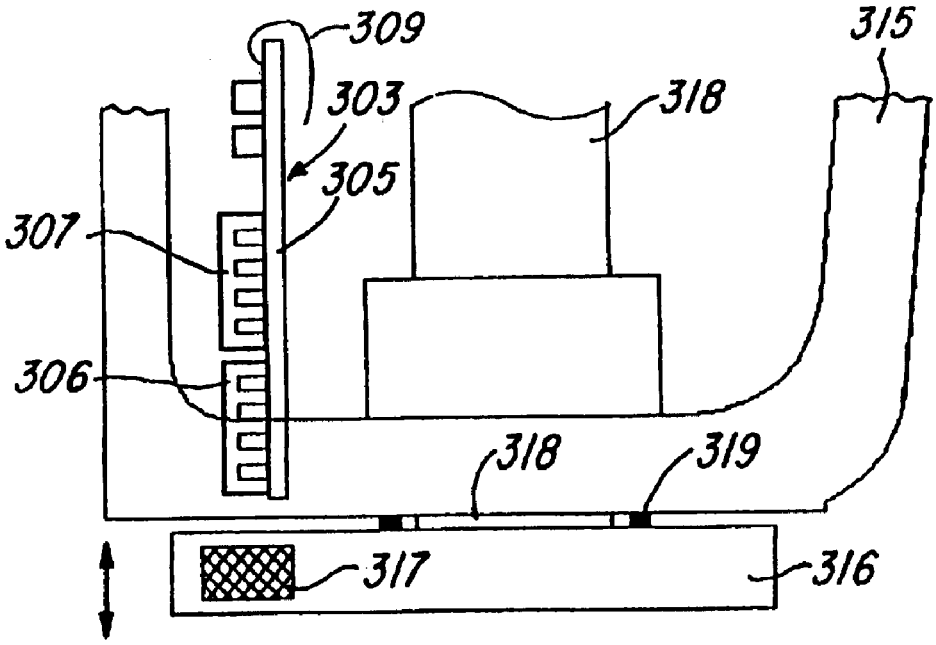
FIG. 27 illustrates diagrammatically a magnetic weight sensor assembly constructed in accordance with a modification of the invention and its use on a knee control unit.

FIG. 27 shows a weight bearing heal sensor example. A bottom attachment plate 316 of the knee control contains a high output magnet 317. The mounting plate is attached to a rod 318 which allows easy sliding movement between a lower knee control assembly 315 and the plate 316. A 50 pound spring 319 surrounds the rod 318 and biases the plate 316 downwardly to its fully extended position of about a 0.040 inch travel. When the patient's weight is not being applied, the maximum air gap is seen between the magnet 317 and the GMR sensor bridge IC 306 having its signal conditioned by the instrumentation amplifier 307. The signal level is transmitted to the microprocessor controller card using the cable assembly 309 for further signal conditioning and for conversion to a usable digital value for use in the closed-loop control. As the patient applies weight to the knee control in the stance phase of his/her gait, the compression of the spring 319 decreases the distance between the magnet 317 and the GMR sensor 306 for increasing the electrical signal level to its maximum at approximately 50 pounds of applied force.

Figure 29:
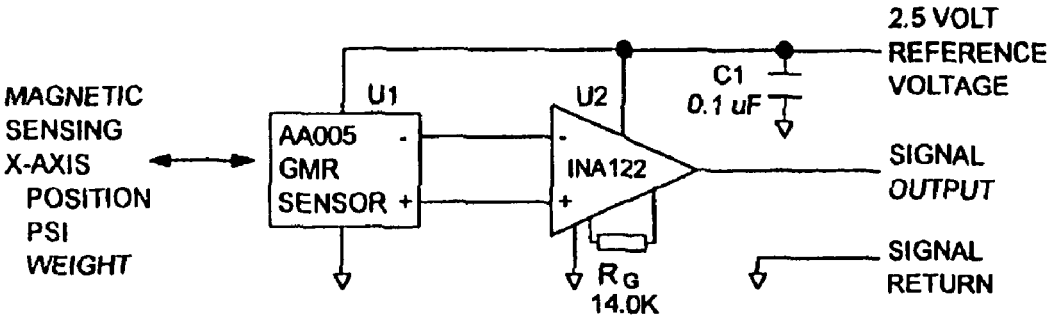
FIG. 29 is a circuit diagram for the GMR magnetic sensor card assemblies shown in FIGS. 25B, 26 and 27.

The sensor remote assembly circuitry is shown on FIG. 29. The magnetic field is detected and measured by a Magnetoresistive GMR 5 kilo-ohm 100 oersted sensitivity bridge manufactured by Nonvolatile Electronics as part number AA005, and designated as UI. The bridge is excited by a precision 2.5 voltage reference. The same 2.5 volt reference is applied to a Burr-Brown INA122 designated as a U2 instrumentation micro-powered amplifier. The instrumentation amplifier uses a 14K gain resistor RG which converts the low level differential GMR bridge output into a 19.29 times increased level. The amplifier also conditions the signal to a low impedance drive level for transmitting to the main microprocessor control card in a low noise manner. Capacitor C1 is used as a power noise decoupler, and the output signal is at a level of 0–2.5 volts. The maximum magnet to sensor distance is selected to obtain a minimum amplifier output voltage of 1.25 volts thus transmitting the usable voltage range of 1.25V to 2.5V.

Figure 30:
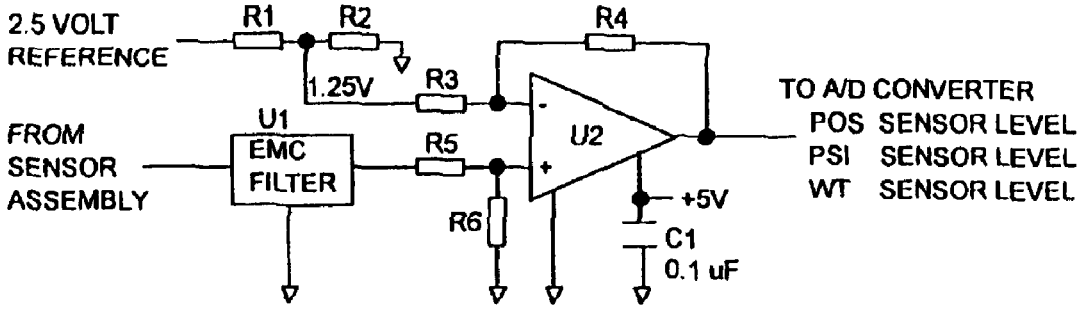
FIG. 30 is a circuit diagram for the three GMR magnetic signal conditioner input circuits.

FIG. 30 shows a common sensor input signal conditioning circuitry for the position, fluid pressure and weight sensors to the microprocessor control card containing three or four identical circuits. In FIG. 30, a common signal conditioning is reduced to 1.25 volts by a resistor voltage divider R1 and R2. The sensor signal is amplified with a gain of 2 by the differential operational amplifier U2. Resistors R4 and R6 are twice the valve of resistors R3 and R5, and the 1.25 volt level is connected to the inverting amplifier input. The sensor input is passed through an EMC low pass filter U1 to reduce significantly the microprocessor's card emissions to the environment and to reduce significantly the environment's emission effects on the microcontroller. The filtered signal is connected to the non-inverting amplifier input through resistor R5. The resultant signal produced is a 0–2.5 volt level free of the 1.25 volt offset. This signal is applied to one of the four inputs of a 12 bit analog-to-digital converter using the same 2.5 volt precision reference.

Figure 28:
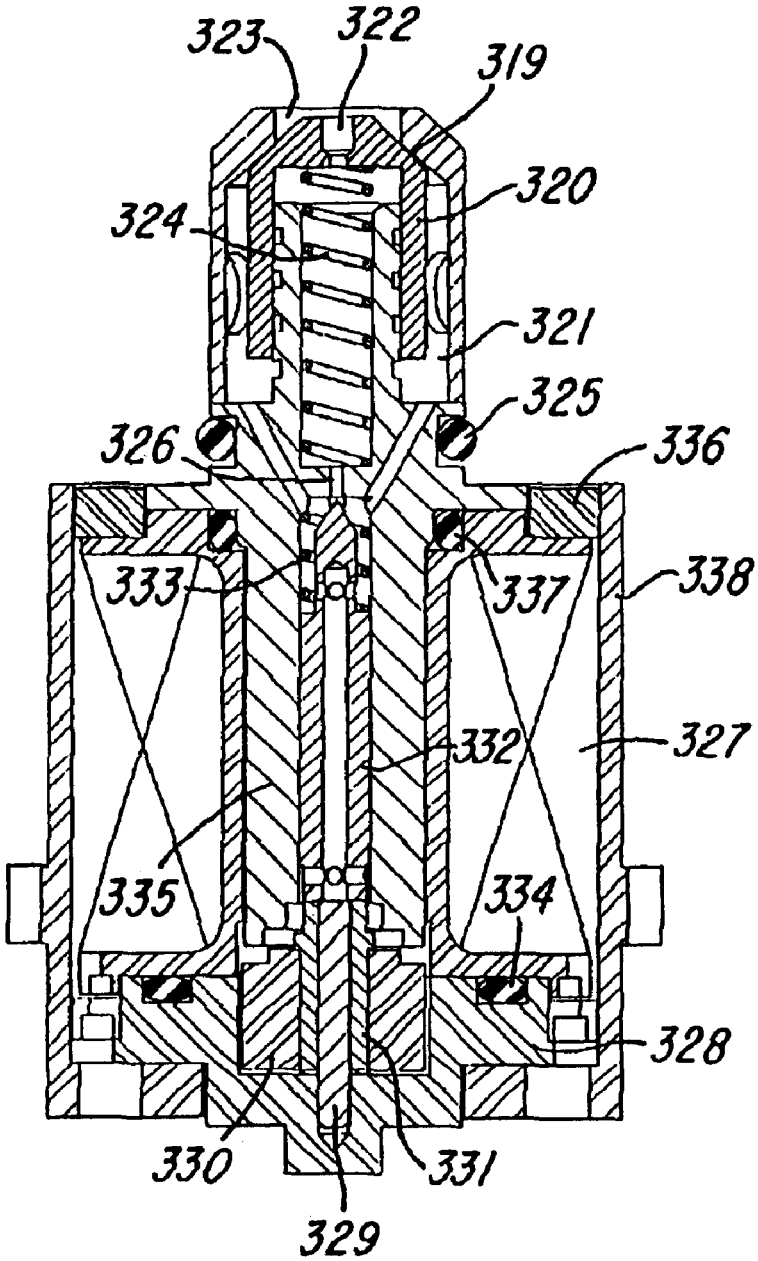
FIG. 28 is an axial section of a two stage pilot operated poppet valve assembly constructed in accordance with a modification of the invention.

In place of the valve described above in FIG. 10, a two stage proportional electronically controlled pilot operated valve is used as an alternate in the electronic knee control and is shown in FIG. 28. The valve has two stages, a main stage poppet valve 320 which controls pressure for the main flow and a normally open pilot stage needle 332 to control the pressure and flow used to control the main stage. The magnetic force applied by a solenoid coil 327 directly controls or closes the needle valve 332 which is subject to relatively small hydraulic forces but regulates the larger hydraulic forces acting on the valve 320. The flow is unidirectional through the valve assembly regardless of the direction of actuator 300 and uses an arrangement of four check valves in a bridge. High pressure fluid flows over the seat 319 from the first or high pressure orifice 323 and past the poppet valve 320 and also through an orifice 322 into a chamber connected through the pilot valve and eight ports to an annular chamber 321 on the low pressure side of the valve. The resistance of the poppet valve 320 to this flow determines the torque resistance generated by the rotary actuator (FIG. 5).

The pilot stage needle valve 332 is biased towards an open position by a spring 333 and controls fluid flowing through an orifice 326. The electromagnetic force acts mechanically through a steel armature 330 and is applied for closing the needle valve 332 for resisting flow, resulting in a proportional increase of pilot fluid pressure. This fluid pressure acts on the main poppet 320 to increase the system pressure. The main stage has two moving parts, the poppet valve 320 and a bias spring 324. The clearance between the poppet valve bore and its support spool is very small such as 0.0005 inch on the diameter in order to minimize pressure and flow losses due to leakage.

The forces acting on the main poppet valve 320 are relatively large but provide for smooth motion, low leakage and rapid response with a relative weak bias spring 324. The pilot stage has the moving parts of steel armature 330 and needle valve 332 and a compression spring 333. The armature 330 is mounted on a nonferrous or aluminum cylindrical pusher tube 331 that slides axially on a ground pin 329. The concentricity of these pieces with a bore in a flux plate 328 and a good surface finish between these pieces minimizes the friction of the pusher tube 331 and consequently minimize system hysterisis, helps repeatability and maximizes the efficiency of the magnetic system.

The pilot needle valve 332 moves relative to the pilot orifice 326 for reducing its effective flow area and resulting in an increase in pilot pressure. The smooth surface finish of the needle and the bore and the relatively close radial clearance between them minimize effects due to side loading from angular or radial misalignment of the needle and pusher tube 331. This helps reduce hysterisis and improves armature efficiency. The magnetic field is carried through a steel core 335, steel flux ring 336, steel case 338 and steel flux plate 328. These components are designed in accordance with dimensional requirements of the electromagnetic forces required for the system. A set of O-ring seals 325, 334 and 337 are used to keep the high pressure hydraulic fluid from leaking into the outside environment.

From the drawings and the above description, it is apparent that a device or apparatus constructed in accordance with the present invention, provides desirable features and advantages. For example, by sensing the differential pressure across the movable hydraulic actuator member and using this differential pressure in a computer controlled closed-loop system for the valve which controls the flow of hydraulic fluid to the actuator, a precisely controlled variable resistance is obtained regardless of variations in manufacturing tolerances, wear of parts, or variations in the viscosity of the hydraulic fluid. Thus apparatus constructed in accordance with the invention is ideally suited for producing a precise knee gait damping resistance for a knee prosthesis without returning by the patient or prosthetist.

As another advantage, the magnetic rotary or linear position sensor, pressure sensor and weight bearing sensor described in connection with FIGS. 25A–27 provide low cost, highly accurate and repeatable results without any mechanical connections. The sensors are also substantially less sensitive to poor environmental conditions such as particles or dirt in the air, and further provide a low noise/high signal transmission to the controlling microprocessor. In addition, the pilot operated two stage solenoid valve described in connection with FIG. 28 provides for controlling a high pressure hydraulic fluid flow, for example, 900 psi at 1.5 gpm, with very low power consumption, such as only 0.1 watt. This feature is ideally suited for a prosthetic knee control where light weight, small size and very low power consumption of rechargeable batteries, are highly desirable.

While the methods and forms of apparatus or devices herein described constitute preferred embodiments of the invention, it is to be understood that the invention is not limited to the precise methods and forms described, and that changes may be made therein without departing from the scope and spirit of the invention as defined in the appended claims.

The invention having been described, the following is claimed:

1. A device for producing a controlled variable resistance to apparatus including a first member moveable relative to a second member, said device comprising hydraulic actuator connecting said first member to said second member, said actuator including a housing enclosing a moveable resistance applying member separating a first chamber and a second chamber within said housing, hydraulic fluid passages connected to said chambers, hydraulic fluid within said chambers and said passages, a solenoid controlled valve connected to control the flow of hydraulic fluid through said passages, a magnet and a magnetically actuated electronic sensor arranged to sense changes in the hydraulic fluid pressure within at least one of said chambers, and a computer controlled electronic system responsive to said sensor for actuating said valve to control precisely the flow of said fluid through said valve and into and out of said first and second chambers.

2. A device as defined in claim 1 and including a position sensor for sensing the position of said first member relative to said second member and connected to said control system for applying a predetermined resistance profile to the device.

3. A device as defined in claim 2 wherein said position sensor comprises a second magnet and a second magnetically actuated electronic sensor, and a relatively moveable variable shutter spaced between said second magnet and said second electronic sensor for varying the magnetic field in response to relative movement between said first and second members.

4. A device as defined in claim 1 and including means for biasing the flow of hydraulic fluid through said valve between said first chamber and said second chamber.

5. A device as defined in claim 1 and including a first connector for connecting said first member to a partial leg of an amputee and a second connector for connecting said second member to an artificial foot for the amputee.

6. A device as defined in claim 5 wherein said control system includes an electronic sensor for sensing the force exerted on said second connector by the artificial foot while the amputee is walking.

7. A device as defined in claim 1 wherein said resistance applying member comprises a rotary shaft connected to a vane type rotor within said housing, and an endless flexible sealing member extending around said rotor and engaging said housing.

8. A device as defined in claim 1 wherein said solenoid valve comprises a two stage pilot operated valve connected to said fluid passages.

9. A device as defined in claim 1 wherein said magnet is positioned within one of said passages with a spring bias for simultaneously sensing the hydraulic fluid pressure within said first and second chambers, and said electronic sensor is positioned out of communication with said fluid and is responsive to movement of said magnet.

10. A device for producing a controlled variable resistance to apparatus including a first member moveable relative to a second member, said device comprising hydraulic actuator connecting said first member to said second member, said actuator including a housing enclosing a moveable resistance applying member separating a first chamber and a second chamber within said housing, hydraulic fluid passages connected to said chambers, hydraulic fluid within said chambers and said passages, a two stage pilot operated solenoid valve connected to control the flow of hydraulic fluid through said passages, an electronic sensor arranged to sense changes in the hydraulic fluid pressure within at least one of said chambers, and a computer controlled electronic system responsive to said sensor for actuating said valve to control precisely the flow of said fluid through said valve and into and out of said first and second chambers.

11. A device as defined in claim 10 and including a position sensor for sensing the position of said first member relative to said second member and connected to said control system for applying a predetermined resistance profile to said device.

12. A device as defined in claim 11 wherein said position sensor comprises a magnet and a magnetically actuated electronic sensor, and a relatively moveable variable shutter spaced between said magnet and said electronic sensor for varying the magnetic field in response to relative movement between said first and second members.

13. A device as defined in claim 10 and including a first connector for connecting said first member to a partial leg of an amputee and a second connector for connecting said second member to an artificial foot for the amputee.

14. A device as defined in claim 13 and including a magnet and a magnetically actuated electronic sensor for sensing the force exerted on said second connector by the artificial foot while the amputee is walking.

15. A device as defined in claim 10 wherein said resistance applying member comprises a rotary shaft connected to a vane type rotor within said housing, and an endless flexible sealing member extending within a groove around said rotor and engaging said housing.

16. A device as defined in claim 10 and including a magnet positioned within one of said passages with a spring bias for simultaneously sensing the hydraulic fluid pressure within said first and second chambers, and said electronic sensor is positioned out of communication with said fluid and is responsive to movement of said magnet.

17. A device adopted for producing a controlled variable resistance to apparatus including a first member moveable relative to a second member, an actuator connecting said first member to said second member, said device comprising a housing enclosing a moveable displacement member separating a first chamber and a second chamber within said housing, fluid passages connected to said chambers and a fluid within said chambers and said passages, a solenoid controlled valve connected to control the flow of fluid through said passages, a position sensor for sensing the position of said first member relative to said second member and including a magnet and a magnetically actuated electronic sensor, a variable shutter connected for movement with said first member and spaced between said magnet and said electronic sensor for variably restricting the magnetic field in response to relative movement between said first and second members, and a computer controlled electronic system responsive to said sensor for actuating said valve to control the flow of said fluid through said valve and into and out of said first and second chambers.

*18. A method of controlling a prosthetic knee worn by a patient, the prosthetic knee containing fluid used at least in part to control the movement of the knee, the method comprising:*

*measuring fluid pressure of the prosthetic knee;*

*measuring movement characteristics of the prosthetic knee;*

*calculating a desired fluid pressure based on at least the measured movement characteristics; and*

*adjusting fluid pressure based on a comparison of the calculated desired fluid pressure with the measured fluid pressure.*

*19. The method of claim 18, wherein measuring movement characteristics comprises measuring a moving direction of the prosthetic knee.*

*20. The method of claim 18, wherein measuring movement characteristics comprises measuring a moving velocity of the prosthetic knee.*

*21. A prosthetic knee adapted to be worn by a patient, the prosthetic knee comprising:*

*movement characteristic sensors that measure movement characteristics of the prosthetic knee;*

*a chamber comprising fluid that at least partially controls the movement of the prosthetic knee;*

*a fluid pressure sensor in communication with the fluid for measuring the pressure of the fluid; and*

*an electronic control unit that calculates a desired fluid pressure based on at least the measured movement characteristics of the prosthetic knee and that adjusts fluid pressure based on a comparison of the calculated desired fluid pressure with the measured fluid pressure.*

* * * * *